US012716894B2

(12) United States Patent
Kuenstner et al.

(10) Patent No.: US 12,716,894 B2
(45) Date of Patent: Aug. 25, 2026

(54) COMBINATORIAL MAP ANTIBODY TESTS FOR DETECTION AND DIAGNOSIS

(71) Applicant: Temple University—Of The Commonwealth System of Higher Education, Philadelphia, PA (US)

(72) Inventors: John Todd Kuenstner, Abington, PA (US); Raghava Potula, Dresher, PA (US)

(73) Assignee: Temple University—Of The Commonwealth System of Higher Education, Philadelphia, PA (US)

(*) Notice: Subject to any disclaimer, the term of this patent is extended or adjusted under 35 U.S.C. 154(b) by 1103 days.

(21) Appl. No.: 17/781,886

(22) PCT Filed: Dec. 1, 2020

(86) PCT No.: PCT/US2020/062642

§ 371 (c)(1),
(2) Date: Jun. 2, 2022

(87) PCT Pub. No.: WO2021/113199

PCT Pub. Date: Jun. 10, 2021

(65) Prior Publication Data

US 2023/0019261 A1 Jan. 19, 2023

Related U.S. Application Data

(60) Provisional application No. 62/942,480, filed on Dec. 2, 2019.

(51) Int. Cl.
*G01N 33/53* (2006.01)
*G01N 33/564* (2006.01)

(52) U.S. Cl.
CPC ....... *G01N 33/564* (2013.01); *G01N 2333/35* (2013.01); *G01N 2333/912* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 7,488,580 | B1 * | 2/2009 | Naser | C12Q 1/689 435/6.16 |
| 2004/0175695 | A1 | 9/2004 | Debad | |
| 2004/0248158 | A1 * | 12/2004 | Loughran, Jr. | G01N 33/564 435/6.16 |
| 2011/0311563 | A1 * | 12/2011 | Reyrat | C07K 14/35 435/7.92 |
| 2018/0252710 | A1 * | 9/2018 | Zhang | G01N 33/564 |

FOREIGN PATENT DOCUMENTS

| | | |
|---|---|---|
| EP | 2052737 | 4/2009 |
| EP | 2089712 | 8/2009 |
| WO | 2008064336 | 5/2008 |

OTHER PUBLICATIONS

Jorgensen et al., Active Crohn's disease is associated with low vitamin D levels, Journal of Crohn's and Colitis, 2013, 7, 3407-e415. (Year: 2013).*

Bach et al., Immunogenicity of *Mycobacterium avium* subsp. paratuberculosis proteins in Crohn's disease patients, Scandinavian Journal If Gastroenterology, 2011; 46: pp. 30-39. (Year: 2011).*

Van Der Vekiens et al., Human and equine cardiovascular endocrinology: beware to compare, Cardiovascular Endocrinology 2013, vol. 2, No. 4, pp. 67-76. (Year: 2013).*

Torzewski et al., Animal Models of C-Reactive Protein, Hindawl Publishing Corporation, Mediators of Inflammation, vol. 2014, Article ID 683598, 2014, pp. 1-7. (Year: 2014).*

Zhang, P., et al., "Serological Testing for Mycobacterial Heat Shock Protein Hsp65 Antibody in Health and Diseases", Microorganisms, 2019, 8, 47.

Abubakar, I., et al., "Detection of Mycobacterium avium subspecies paratuberculosis from patients with Crohn's disease using nucleic acid-based techniques: A systematic review and meta-analysis", Inflamm Bowel Dis, 2008, 14: 401-410.

Arru, G., et al., "Is there a role for *Mycobacterium avium* subspecies paratuberculosis in Parkinson's disease?", J Neuroimmunol, 2016, 293: 86-90.

Bach, H., et al., "Immunogenicity of *Mycobacterium avium* subsp. paratuberculosis proteins in Crohn's disease patients", Scand J Gastroenterol, 2011, 46: 30-39.

Bach, H., et al., "Mycobacterium tuberculosis virulence is mediated by PtpA dephosphorylation of human vacuolar protein sorting 33B", Cell Host Microbe, 2008, 3: 316-322.

Bach, H., et al., "Protein Kinase G Induces an Immune Response in Cows Exposed to *Mycobacterium avium* Subsp. paratuberculosis", Biomed Res Int, 2018, 2018: 1450828 (pp. 1-9).

Bernstein, C.N., et al., "Population-based case control study of seroprevalence of Mycobacterium paratuberculosis in patients with Crohn's disease and ulcerative colitis", J Clin Microbiol, 2004, 42: 1129-1135.

Biet, F., et al., "Serum antibodies to *Mycobacterium avium* subspecies paratuberculosis combined with anti-*Saccharomyces cerevisiae* antibodies in Crohn's disease patients: Prevalence and diagnostic role", Dig Dis Sci, 2011, 56: 1794-1800.

Bo, M., et al., "Association between Lipoprotein Levels and Humoral Reactivity to *Mycobacterium avium* subsp. paratuberculosis in Multiple Sclerosis, Type 1 Diabetes Mellitus and Rheumatoid Arthritis", Microorganisms, 2019, 7 (pp. 1-11).

(Continued)

*Primary Examiner* — Gary Counts
(74) *Attorney, Agent, or Firm* — Riverside Law LLP

(57) ABSTRACT

The present disclosure provides kits for detecting *Mycobacterium avium* subspecies paratuberculosis (MAP) infection and biomarkers correlated with MAP-associated diseases or disorders. The present disclosure also provides methods of diagnosing a subject with a MAP-associated autoimmune disease or disorder and/or determining the treatment course of a subject diagnosed with a MAP-associated autoimmune disease or disorder.

7 Claims, 16 Drawing Sheets

(56) References Cited

OTHER PUBLICATIONS

Bo, M., et al., "IL-2 and Mycobacterial Lipoarabinomannan as Targets of Immune Responses in Multiple Sclerosis Patients", Microorganisms, 2020, 8.
Bo, M., et al., "Interferon regulatory factor 5 is a potential target of autoimmune response triggered by Epstein-barr virus and *Mycobacterium avium* subsp. paratuberculosis in rheumatoid arthritis: Investigating a mechanism of molecular mimicry", Clin Exp Rheumatol, 2018, 36: 376-381.
Bo, M., et al., "PtpA and PknG Proteins Secreted by *Mycobacterium avium* subsp. paratuberculosis are Recognized by Sera from Patients with Rheumatoid Arthritis: A Case-Control Study", J Inflamm Res, 2019, 12: 301-308.
Bull, T.J., et al., "Detection and verification of *Mycobacterium avium* subsp. paratuberculosis in fresh ileocolonic mucosal biopsy specimens from individuals with and without Crohn's disease", J Clin Microbiol, 2003, 41: 2915-2923.
Bull, T.J., et al., "Improved Culture Medium (TiKa) for *Mycobacterium avium* Subspecies paratuberculosis (MAP) Matches qPCR Sensitivity and Reveals Significant Proportions of Non-viable MAP in Lymphoid Tissue of Vaccinated MAP Challenged Animals", Front Microbiol, 2016, 7: 2112.
Chacon, O., et al., "Johne's disease, inflammatory bowel disease, and Mycobacterium paratuberculosis", Annu Rev Microbiol, 2004, 58: 329-363.
Cossu, D., et al., "From Sardinia to Japan: Update on the role of MAP in multiple sclerosis", Future Microbiol, 2019, 14: 643-646.
Cossu, D., et al., "Human interferon regulatory factor 5 homologous epitopes of Epstein-Barr virus and *Mycobacterium avium* subsp. paratuberculosis induce a specific humoral and cellular immune response in multiple sclerosis patients", Mult Scler, 2015, 21: 984-995.
Cossu, D., et al., "Humoral response against host-mimetic homologous epitopes of *Mycobacterium avium* subsp. paratuberculosis in Japanese multiple sclerosis patients", Sci Rep, 2016, 6: 29227.
Dow, C.T., et al., "Cows Get Crohn's Disease and They're Giving US Diabetes", Microorganisms, 2019, 7 (pp. 1-10).
Ellingson, J.L., et al., "Detection of viable *Mycobacterium avium* subsp. paratuberculosis in retail pasteurized whole milk by two culture methods and PCR", J Food Prot, 2005, 68: 966-972.
Euesden, J., et al., "A bidirectional relationship between depression and the autoimmune disorders—New perspectives from the National Child Development Study", PLoS One, 2017, 12: e0173015 (pp. 1-14).
Feller, M., et al., "*Mycobacterium avium* subspecies paratuberculosis and Crohn's disease: A systematic review and meta-analysis", Lancet Infect Dis, 2007, 7: 607-613.
Foddai, A., et al., "Optimization of a phage amplification assay to permit accurate enumeration of viable *Mycobacterium avium* subsp. paratuberculosis cells", Appl Environ Microbiol, 2009, 75: 3896-3902.
Frau, J., et al., "Combining HLA-DRB1-DQB1 and *Mycobacterium avium* Subspecies Paratubercolosis (MAP) antibodies in Sardinian multiple sclerosis patients: Associated or independent risk factors?", BMC Neurol, 2016, 16: 148.
Frau, J., et al., "Role of interferon-beta in *Mycobacterium avium* subspecies paratuberculosis antibody response in Sardinian MS patients", J Neurol Sci, 2015, 349: 249-250.
Graham, D.Y. "RHB-104, a Fixed-Dose, Oral Antibiotic Combination against Mycobacterium Avium Paratuberculosis (MAP) Infection, Is Effective in Moderately to Severely Active Crohn's Disease", In Proceedings of the Annual Scientific Meeting and Postgraduate Course (ACG), San Antonio, TX, USA, 2019; pp. 25-30.
Grant, I.R., et al., "Incidence of Mycobacterium paratuberculosis in bulk raw and commercially pasteurized cows' milk from approved dairy processing establishments in the United Kingdom", Appl Environ Microbiol, 2002, 68: 2428-2435.
Grant, I.R., et al., "Viable *Mycobacterium avium* ssp. paratuberculosis isolated from calf milk replacer", J Dairy Sci, 2017, 100: 9723-9735.
Hesam Shariati, S., et al., "Detection of *Mycobacterium avium* subsp. paratuberculosis in Iranian patients with type 1 diabetes mellitus by PCR and ELISA", J Infect Dev Ctries, 2016, 10: 857-862.
Kuenstner, J.T., et al., "The Consensus from the *Mycobacterium avium* ssp. paratuberculosis (MAP) Conference 2017", Front Public Health, 2017, 5: 208.
Li, H., et al., "The Sequence Alignment/Map format and SAMtools", Bioinformatics, 2009, 25(16):2078-2079.
Lichtenstein GR, et al., "ACG Clinical Guideline: Management of Crohn's Disease in Adults", Am J Gastroenterol. 2018, 113(4):481-517.
Lin, T.M., et al., "Autoimmune rheumatic diseases increase dementia risk in middle-aged patients: A nationwide cohort study", PLoS One, 2018, 13: e0186475 (pp. 1-12).
Magombedze, G., et al., "Evalution of the "Iceberg Phenomenon" in Johne's Disease through Mathematical Modelling" PLoS One, 2013, 8: e76636 (pp. 1-11).
Mameli, G., et al., "Epstein Barr Virus and *Mycobacterium avium* subsp. paratuberculosis peptides are recognized in sera and cerebrospinal fluid of MS patients", Sci Rep, 2016, 6: 22401.
Mameli, G., et al., "Immune response induced by Epstein-Barr virus and *Mycobacterium avium* subsp. paratuberculosis peptides in current and past infectious mononucleosis: A risk for multiple sclerosis? ", Eur J Neurol, 2016, 23: 140-147.
Masala, S., et al., "Proinsulin and MAP3865c homologous epitopes are a target of antibody response in new-onset type 1 diabetes children from continental Italy", Pediatr Diabetes, 2015, 16: 189-195.
Naser, A., et al., "Polymorphisms in TNF Receptor Superfamily 1B (TNFRSF1B:rs3397) are Linked to *Mycobacterium avium* paratuberculosis Infection and Osteoporosis in Rheumatoid Arthritis", Microorganisms, 2019, 7, 646.
Naser, S.A., et al., "Culture of *Mycobacterium avium* subspecies paratuberculosis (MAP) from the blood of patients with Crohn's disease: A follow-up blind multi center investigation", The Open Inflammation Journal, 2009, 2: 22-23.
Naser, S.A., et al., "Culture of *Mycobacterium avium* subspecies paratuberculosis from the blood of patients with Crohn's disease", Lancet, 2004, 364: 1039-1044.
Niegowska, M., et al., "Antibodies against Proinsulin and Homologous MAP Epitopes Are Detectable in Hashimoto's Thyroiditis Sardinian Patients, an Additional Link of Association", PLoS One, 2015, 10: e0133497 (pp. 1-11).
Niegowska, M., et al., "Seroreactivity against Specific L5P Antigen from *Mycobacterium avium* subsp. paratuberculosis in Children at Risk for T1D", PLoS One, 2016, 11: e0157962 (pp. 1-10).
Niegowska, M., et al., "Type 1 Diabetes at-risk children highly recognize *Mycobacterium avium* subspecies paratuberculosis epitopes homologous to human Znt8 and Proinsulin", Sci Rep, 2016, 6: 22266 (pp. 1-10).
Over, K., et al., "Current perspectives on *Mycobacterium avium* subsp. paratuberculosis, Johne's disease, and Crohn's disease: A review", Crit Rev Microbiol, 2011, 37: 141-156.
PF Pinsky and CS Zhu, "Building multi-marker algorithms for disease prediction—the role of correlations among markers", Biomarker Insights 2011:6 83-93.
Pozzato, N., et al., "Evaluation of a rapid and inexpensive liquid culture system for the detection of *Mycobacterium avium* subsp. paratuberculosis in bovine faeces", J Microbiol Methods, 2011, 84: 413-417.
Rathnaiah, G., et al., "Pathogenesis, Molecular Genetics, and Genomics of *Mycobacterium avium* subsp. paratuberculosis, the Etiologic Agent of Johne's Disease", Front Vet Sci, 2017, 4: 187.
Singh, S.H., et al., "First Mass Screening of the Human Population to Estimate the Bio-load of *Mycobacterium avium* Subspecies paratuberculosis in North India", Journal of Biological Sciences, 2014, 14: 237-247.

(56) References Cited

OTHER PUBLICATIONS

Slavin, Y.N., et al., "High levels of antibodies against PtpA and PknG secreted by *Mycobacterium avium* ssp. paratuberculosis are present in neuromyelitis optica spectrum disorder and multiple sclerosis patients", J Neuroimmunol, 2018, 323: 49-52.
Swift, B.M., et al., "Evidence of Mycobacterium tuberculosis complex bacteraemia in intradermal skin test positive cattle detected using phage-RPA", Virulence, 2016, 7: 779-788.
Witney, A.A., et al., "Clinical use of whole genome sequencing for Mycobacterium tuberculosis", BMC Med, 2016, 14, 46.

* cited by examiner

| Variable | CD patients (2 also had UC) (n = 61) | UC patients only (n = 14) | Non-CD patients (including UC only subjects) (n = 140) |
|---|---|---|---|
| Age, N | 61 | 13 | 130 |
| Mean (SD) | 46.2 (15.5) | 44.1 (17.3) | 52.6 (17.4) |
| Median (Range) | 47.0 (21.0-72.0) | 42.0 (24.0-80.0) | 57.5 (17.0-85.0) |
| Gender, N (%) | | | |
| Female | 33 (54.1%) | 7 (50.0%) | 82 (58.6%) |
| Male | 28 (45.9%) | 7 (50.0%) | 58 (41.4%) |
| HB Index, N | 60 | 13 | NA |
| Mean (SD) | 2.4 (2.0) | 1.5 (1.8) | NA |
| Median (Range) | 2.0 (0.0-7.0) | 1.0 (0.0-5.0) | NA |

Fig. 1

| Subject category | Detection Method | | | |
|---|---|---|---|---|
| | Phage Assay | Pozzato Culture | TiKa Culture† | MGIT Culture |
| CD* (n = 61) | 28, 46% | 35, 57% | 22, 36% | 15, 25% |
| UC only (n = 14) | 6, 43% | 10, 71% | 1, 7% | 4, 29% |
| Non-CD** (n = 140) | 85, 61% | 89, 64% | 42, 30% | 21, 15% |
| All subjects (n=201) | 113, 56% | 124, 62% | 64, 32% | 36, 18% |

Fig. 2

| Variable | N | CD patients (n=61) | Non-CD patients (n=140) | Odds Ratio | Fisher's exact p-value |
|---|---|---|---|---|---|
| Age, overall | 191 | 61 (31.9%) | 130 (68.1%) | | 0.003 |
| <=52 | 91 | 39 (42.9%) | 52 (57.1%) | 2.66 (1.42, 4.99) | |
| >52 | 100 | 22 (22.0%) | 78 (78.0%) | Reference | |
| Gender, overall | 201 | 61 (30.3%) | 140 (69.7%) | | 0.64 |
| Male | 86 | 28 (32.6%) | 58 (67.4%) | 1.20 (0.65, 2.20) | |
| Female | 115 | 33 (28.7%) | 82 (71.3%) | Reference | |
| MGIT Culture, overall | 201 | 61 (30.3%) | 140 (69.7%) | | 0.11 |
| Positive | 36 | 15 (41.7%) | 21 (58.3%) | 1.85 (0.88, 3.89) | |
| Negative | 165 | 46 (27.9%) | 119 (72.1%) | Reference | |
| TiKa Culture, overall | 199 | 60 (30.2%) | 139 (69.8%) | | 0.41 |
| Positive | 64 | 22 (34.4%) | 42 (65.6%) | 1.34 (0.71, 2.53) | |
| Negative | 135 | 38 (28.1%) | 97 (71.9%) | Reference | |
| Pozzato Culture, overall | 201 | 61 (30.3%) | 140 (69.7%) | | 0.43 |
| Negative | 77 | 26 (33.8%) | 51 (66.2%) | 1.30 (0.70, 2.39) | |
| Positive | 124 | 35 (28.2%) | 89 (71.8%) | Reference | |
| Phage Assay, overall | 201 | 61 (30.3%) | 140 (69.7%) | | 0.064 |
| Negative | 88 | 33 (37.5%) | 55 (62.5%) | 1.82 (0.99, 3.34) | |
| Positive | 113 | 28 (24.8%) | 85 (75.2%) | Reference | |
| Hsp65 Antibody, overall | 201 | 61 (30.3%) | 140 (69.7%) | | 0.020 |
| >0.74 | 89 | 35 (39.3%) | 54 (60.7%) | 2.14 (1.16, 3.95) | |
| <=0.74 | 112 | 26 (23.2%) | 86 (76.8%) | Reference | |
| PknG Antibody, overall | 200 | 61 (30.5%) | 139 (69.5%) | | 0.35 |
| Negative | 120 | 40 (33.3%) | 80 (66.7%) | 1.40 (0.75, 2.63) | |
| Positive | 80 | 21 (26.3%) | 59 (73.8%) | Reference | |
| PtpA Antibody, overall | 200 | 61 (30.5%) | 139 (69.5%) | | 0.73 |
| Negative | 146 | 46 (31.5%) | 100 (68.5%) | 1.20 (0.60, 2.39) | |
| Positive | 54 | 15 (27.8%) | 39 (72.2%) | Reference | |
| MAP IDEXX Ab, overall | 201 | 61 (30.3%) | 140 (69.7%) | | 0.62 |
| Positive | 135 | 43 (31.9%) | 92 (68.1%) | 1.25 (0.65, 2.39) | |
| Negative | 66 | 18 (27.3%) | 48 (72.7%) | Reference | |

Fig. 6

| Assay Method | CD vs. Non-CD | | | CD+UC vs. Non-CD+UC | | |
|---|---|---|---|---|---|---|
| | n | Adjusted Odds Ratio (95% CI) | p-value | n | Adjusted Odds Ratio (95% CI) | p-value |
| Using Culture only | 191 | | | 191 | | |
| MGIT Culture (+ vs. -) | | 2.36 (1.06,5.28) | 0.037 | | 3.19 (1.40, 7.23) | 0.006 |
| Using Antibody only | 191 | | | 190 | | |
| Hsp65 Antibody (>0.74 vs. ≤0.74) | | 2.40 (1.25,4.61) | 0.009 | | 1.32 (1.05, 1.67) ‡ | 0.016 |
| PknG Antibody (- vs. +) | | - | NS | | 2.18 (1.12, 4.23) | 0.022 |
| Using both Culture and Antibody | 191 | | | 190 | | |
| MGIT Culture (+ vs. -) | | 2.54 (1.11, 5.81) | 0.027 | | 3.51 (1.51, 8.16) | 0.004 |
| Hsp65 Antibody (>0.74 vs. ≤0.74) | | 2.51 (1.29, 4.88) | 0.007 | | 2.30 (1.19, 4.45) | 0.013 |
| PknG Antibody (- vs. +) | | - | NS | | 2.13 (1.08, 4.20) | 0.030 |

Fig. 8

| Assay | Any culture positive N (%) | All cultures negative N (%) | Total N (%) |
|---|---|---|---|
| Phage assay + (Plaques + IS900) | 131 (65%) | 25 (12%) | 156 (78%) |
| Phage assay Negative | 26 (13%) | 19 (9%) | 45 (22%) |
| Total | 157 (78%) | 44 (22%) | 201 |

Fig. 9

COMBINATORIAL MAP ANTIBODY TESTS FOR DETECTION AND DIAGNOSIS

CROSS-REFERENCE TO RELATED APPLICATIONS

This application is a national phase application filed under 35 U.S.C. § 371 claiming benefit to PCT International Application PCT/US2020/062642, filed Dec. 1 2020, which claims priority to and the benefit of U.S. Provisional Application No. 62/942,480, filed Dec. 2, 2019, the disclosures of which are incorporated herein by reference in their entireties.

BACKGROUND OF THE INVENTION

*Mycobacterium avium* subspecies *paratuberculosis* (MAP) is accepted as the cause of Johne's Disease (JD) (Over, K., et al., *Crit Rev Microbiol,* 2011, 37: 141-156), a chronic diarrheal wasting disease of cattle and a wasting disease in sheep and goats (Rathnaiah, G., et al., *Front Vet Sci,* 2017, 4: 187) and has long been suspected to be involved in the etiology of Crohn's Disease (CD), an inflammatory bowel disease (IBD) of humans (Chacon, O., et al., *Annu Rev Microbiol,* 2004, 58: 329-363). MAP and/or CD are also associated with many other autoimmune diseases including multiple sclerosis (Bo, M., et al, *Microorganisms,* 2020, 8; Cossu, D., et al., *Future Microbiol,* 2019, 14: 643-646; Slavin, Y. N., et al., *J Neuroimmunol,* 2018, 323: 49-52; Frau, J., et al., *BMC Neurol,* 2016, 16: 148; Cossu, D., et al., *Sci Rep,* 2016, 6: 29227; Mameli, G., et al., *Sci Rep,* 2016, 6: 22401; Mameli, G., et al., *Eur J Neurol,* 2016, 23: 140-147; Frau, J., et al., *J Neurol Sci,* 2015, 349: 249-250; Cossu, D., et al., *Mult Scler,* 2015, 21: 984-995), type I diabetes mellitus (Dow, C. T., et al., *Microorganisms,* 2019, 7; Bo, M., et al., *Microorganisms,* 2019, 7; Niegowska, M., et al., *PLoS One,* 2016, 11: e0157962; Hesam Shariati, S., et al., *J Infect Dev Ctries,* 2016, 10: 857-862; Niegowska, M., et al., *Sci Rep,* 2016, 6: 22266; Masala, S., et al., *Pediatr Diabetes,* 2015, 16: 189-195), rheumatoid arthritis (Bo, M., et al., *J Inflamm Res,* 2019, 12: 301-308; Naser, A., et al., *Microorganisms,* 2019, 7; Bo, M., et al., *Clin Exp Rheumatol,* 2018, 36: 376-381), Sjogren's syndrome (Zhang, P., et al., *Microorganisms,* 2019, 8), asymmetric lateral sclerosis (Pierce, E. S., *Med Hypotheses,* 2018, 119: 1-5), celiac disease (Biet, F., et al., *Dig Dis Sci,* 2011, 56: 1794-1800), depression (Euesden, J., et al., *PLoS One,* 2017, 12: e0173015), thyroiditis (Niegowska, M., et al., *PLoS One,* 2015, 10: e0133497), and the neurodegenerative diseases including Alzheimer's disease (Lin, T. M., et al., *PLoS One,* 2018, 13: e0186475) and Parkinson's disease (Arru, G., et al., *J Neuroimmunol,* 2016, 293: 86-90). A diarrheal/wasting illness associated with infection with MAP has also been reported in non-human primates (McClure, H. M., et al., *J Infect Dis,* 1987, 155: 1011-1019).

Viable MAP is present in our food, potable water and can be isolated from commercially available pasteurized milk (Ellingson, J. L., et al., *J Food Prot,* 2005, 68:966-972; Grant, I. R., et al., *Appl Environ Microbiol,* 2002, 68:2428-2435) with MAP being identified in 2.7% of retail pasteurized milk samples purchased in Wisconsin, Minnesota and California, USA (Ellingson, J. L., et al., *J Food Prot,* 2005, 68:966-972). It is highly likely therefore that humans are regularly exposed to this animal pathogen. Screening of human sera with a MAP specific antibody assay has found evidence of MAP specific immune recognition in subjects with a range of underlying diseases including patients with CD and asymptomatic controls (Singh, S. H., et al., *Journal of Biological Sciences,* 2014, 14:237-247). Previous meta-analyses looking predominantly at molecular detection methods also indicated a trend for studies showing a significantly higher percentage of MAP detection in samples from patients with CD, compared to non IBD controls (Abubakar, I., et al., *Inflamm Bowel Dis,* 2008, 14:401-410; Feller, M., et al., *Lancet Infect Dis,* 2007, 7:607-613). However, problems and controversy (page 498 in Lichtenstein G R, Loftus E V Jr, Isaacs, K L, Regueiro, M D, Gerson L B and Sands B E. ACG Clinical Guideline: Management of Crohn's Disease in Adults. nature(dot) com/ajg *Am J Gastroenterol* 2018; 113:481-517; published online 27 Mar. 2018) in proving the association of MAP with any of these conditions has been hampered by definitive and reproducible methods able to detect and grow MAP from humans. Individual smaller studies have cultured MAP from human blood including significantly greater success in CD patients than from controls (Naser, S. A., et al., *Lancet,* 2004, 364:1039-1044; Naser, S. A., et al., *The Open Inflammation Journal,* 2009, 2:22-23). The method used (MGIT ParaTB culture tubes) was not optimal however, requiring three to six months of incubation and being of relatively low reproducibility.

Thus, there is a need in the art for improved systems and methods for detecting MAP and for diagnosing MAP-associated diseases or disorders. This invention satisfies this unmet need.

SUMMARY OF THE INVENTION

In one embodiment, the present invention comprises a kit for use in diagnosing one or more autoimmune disease or disorder, the kit comprising: a) a first assay to detect a biomarker positively correlated with said autoimmune disease or disorder; and b) a second assay to detect a biomarker negatively correlated with said autoimmune disease or disorder.

In one embodiment, said autoimmune disease or disorder to be diagnosed by said kit is one or more selected from the group consisting of: Crohn's Disease (CD), Ulcerative Colitis (UC), Irritable Bowel Syndrome (IBS), Multiple Sclerosis (MS), Type 1 Diabetes Mellitus (T1DM), Sjogren's Syndrome (SS), Systemic Lupus Erythematosus (SLE), Depression, Parkinson's Disease (PD), Alzheimer's Disease (AD), celiac disease, thyroiditis, rheumatoid arthritis, psoriasis, Blau syndrome, lymphangiomatosus and Complex Regional Pain Syndrome (CRPS).

In one embodiment, said biomarker of said first assay in said kit is one or more selected from the group consisting of: an antibody specific for heat shock protein 65 (Hsp65), Hsp65, and a nucleic acid encoding Hsp65. In one embodiment, said first assay comprises a diagnostic device, comprising: a) a first surface area; b) Hsp65 or an antigenic fragment thereof, wherein said Hsp65 or said antigenic fragment thereof is bound to the first surface area; and c) a solution comprising labeled antibodies against said antibody specific for Hsp65.

In one embodiment, said biomarker of said second assay in said kit is one or more selected from the group consisting of: an antibody specific for protein kinase G (PknG), PknG, and a nucleic acid encoding PknG. In one embodiment, said second assay comprises a diagnostic device, comprising: a) a first surface area; b) PknG or an antigenic fragment thereof, wherein said PknG or said antigenic fragment thereof is bound to the first surface area; and c) a solution comprising labeled antibodies against said antibody specific for PknG.

In one embodiment, the kit further comprises a third assay to detect a biomarker associated with MAP infection. In one embodiment, said biomarker of said third assay is or more selected from the group consisting of: an antibody specific for *Mycobacterium avium* subspecies paratuberculosis (MAP) lipopentapetide (L5P), L5P, and a nucleic acid encoding L5P. In one embodiment, said third assay comprises a diagnostic device, comprising: a) a first surface area; b) L5P or an antigenic fragment thereof, wherein said L5P or said antigenic fragment thereof is bound to the first surface area; and c) a solution comprising labeled antibodies against said antibody specific for L5P.

In one embodiment, the present invention comprises a method of diagnosing one or more autoimmune disease or disorder in a subject, the method comprising the steps of: a) detecting a MAP infection in said subject; b) detecting a first biomarker positively correlated with said autoimmune disease or disorder; c) detecting a second biomarker negatively correlated with said autoimmune disease or disorder; and d) diagnosing said subject with said autoimmune disease or disorder if said MAP infection, said first biomarker, and said second biomarker are detected.

In one embodiment, said autoimmune disease or disorder to be diagnosed by said method is one or more selected from the group consisting of: CD, UC, IBS, MS, T1DM, SS, SLE, Depression, PD, AD, celiac disease, thyroiditis, rheumatoid arthritis, psoriasis, Blau syndrome, lymphangiomatosus and CRPS.

In one embodiment, said detecting of a MAP infection of the method further comprises measuring one or more selected from the group consisting of: an antibody specific for L5P, L5P, and a nucleic acid encoding L5P.

In one embodiment, said first biomarker of the method is one or more selected from the group consisting of: an antibody specific for Hsp65, Hsp65, and a nucleic acid encoding Hsp65. In one embodiment, said second biomarker of the method is one or more selected from the group consisting of: an antibody specific for protein kinase G (PknG), PknG, and a nucleic acid encoding PknG.

In one embodiment the method further comprises the step of: administering to said subject diagnosed with one or more autoimmune disease or disorder a therapeutic to treat said one or more autoimmune disease or disorder.

In one embodiment, the present method comprises a method of selecting a subject diagnosed with one or more autoimmune disease or disorder to be treated with one or more antibiotic, the method comprising the steps of: a) detecting a MAP infection in said subject; b) detecting a first biomarker positively correlated with said autoimmune disease or disorder; c) detecting a second biomarker negatively correlated with said autoimmune disease or disorder; d) diagnosing said subject with said autoimmune disease or disorder if said MAP infection, said first biomarker, and said second biomarker are detected; e) detecting the presence of MAP with an additional clinical assay; and f) treating said subject with one or more antibiotic specific to MAP infection if said subject is diagnosed with said autoimmune disease or disorder and MAP is detected in said clinical assay.

In one embodiment, said autoimmune disease or disorder of the method is one or more selected from the group consisting of: CD, UC, IBS, MS, T1DM, SS, SLE, Depression, PD, AD, celiac disease, thyroiditis, rheumatoid arthritis, psoriasis, Blau syndrome, lymphangiomatosus and CRPS.

In one embodiment, said detecting of a MAP infection of said method further comprises measuring one or more selected from the group consisting of: an antibody specific for L5P, L5P, and a nucleic acid encoding L5P.

In one embodiment, said first biomarker of the method is one or more selected from the group consisting of: an antibody specific for Hsp65, Hsp65, and a nucleic acid encoding Hsp65. In one embodiment, said second biomarker of the method is one or more selected from the group consisting of: an antibody specific for protein kinase G (PknG), PknG, and a nucleic acid encoding PknG.

In one embodiment, said clinical assay of the method is one or more selected from the group consisting of: a MAP phage amplification assay, a Pozzato culture assay, a TiKa culture assay, and a Mycobacteria Growth Indicator Tube (MGIT) culture assay.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1 depicts exemplary demographics and clinical characteristics by subgroups for the patients studied in Example 1 (n=201).

FIG. 2 depicts exemplary results demonstrating the analytical sensitivity of MAP detection by phage assay and MGIT, TiKa and Pozzato culture methods among the 201 study subjects. The single asterisk (*) indicates that two CD patients also had diagnosis of UC. Double asterisks (**) indicate that the Non-CD category includes the 14 UC only subjects. The dagger (†) indicates that two subjects had missing TiKa culture results.

FIG. 6 depicts exemplary results demonstrating the association analyses of clinically diagnosed CD patients with covariates of interest.

FIG. 8 depicts exemplary results demonstrating association analyses of MAP culture and serology with occurrence of select disease (CD or CD+UC). Results are reported from six (6) logistic regression models (3 assay method variables inclusion settings×2 select diseases (CD or CD+UC), all adjusted for age (≤52 vs. >52) and gender. NS indicates not significant and the double dagger (‡) indicates the OR and 95% CI for a 0.2-unit increment of Hsp65 antibody.

FIG. 9 depicts exemplary results demonstrating the agreement analysis between Phage assay and culture results (n=201).

FIG. 14, comprising FIG. 14A depicts a boxplot of exemplary results showing Hsp65 Antibody signal in samples from CD donors versus samples from healthy controls. FIG. 14B depicts the marker plot for the logistic regression analysis described in Example 2. FIG. 14C depicts exemplary results demonstrating the receiver operating characteristic (ROC) curve of the logistic regression model for Hsp65 antibody signal categorized by CD donors and healthy controls.

DETAILED DESCRIPTION

Figure 3:
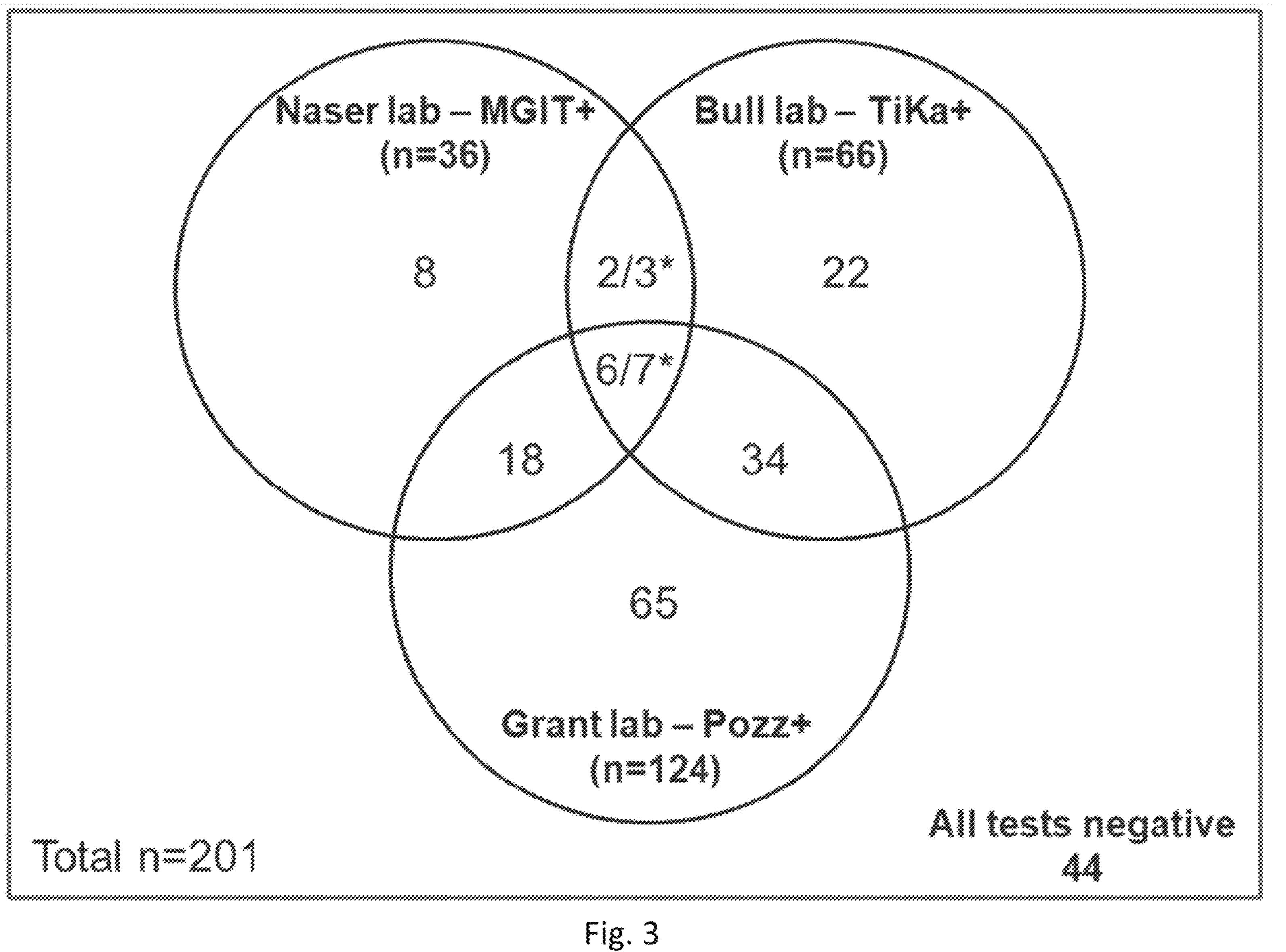
FIG. 3 depicts exemplary results demonstrating interrelationships between the MGIT, TiKa and Pozzato culture methods. The asterisk (*) indicates that there were two samples with "contaminated" results from the Bull lab.

The present invention is based, in part, on the knowledge that MAP infection does not always manifest as a disease or disorder and, therefore, there is a need in the art for improved methods of diagnosing diseases or disorders associated with MAP infection, including autoimmune diseases or disorders. The present invention is also based, in part, upon the novel discovery that certain antibodies are positively or negatively correlated with autoimmune diseases, including Crohn's disease and ulcerative colitis, and that a model combining positively correlated and negatively correlated biomarkers for disease has improved predictive power for diagnosis over either biomarker alone. Further, the present invention is based on the discovery that additional clinical assays to detect MAP infection, used in conjunction with the kits and methods for measuring antibodies of the present invention, further improve the predictability and reliability of diagnosing autoimmune diseases or disorders.

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

A disease or disorder is "alleviated" if the severity of a sign or symptom of the disease or disorder, the frequency with which such a sign or symptom is experienced by a patient, or both, is reduced.

"Accuracy", as used herein, refers to the total proportion of true results (true positive+true negatives) as a measure of the overall degree of veracity of a detection or diagnostic kit and/or method.

An "assay", as used herein, refers to any composition, device, system and/or method to qualitatively and/or quantitatively measure a moiety or substance in a sample. For example, an immunoassay may be used to detect the presence of or measure the quantity of a biomarker (for example, an antibody) in a biological sample (for example, plasma).

An "antigen", as used herein, refers to a molecule that provokes an immune response. This immune response may involve either antibody production, or the activation of specific immunologically-competent cells, or both. The skilled artisan will understand that any macromolecule, including virtually all proteins or peptides, can serve as an antigen. It should be readily apparent to a skilled artisan that an antigen can be generated, synthesized or can be derived from a biological sample. Such a biological sample can include, but is not limited to a tissue sample, a tumor sample, a cell or a biological fluid.

A "biological sample", as used herein, refers to any biologically derived tissue or fluid from which biomarkers of the present invention may be assayed. Examples of such samples include but are not limited to blood, sputum, lymph, lung lavage fluids, urine, gynecological fluids, biopsies, amniotic fluid and smears. Samples that are liquid in nature may be referred to herein as "bodily fluids." Samples may be obtained from a patient by a variety of techniques including, for example, by scraping or swabbing an area or by using a needle to aspirate bodily fluids. Methods for collecting various body samples are well known in the art. Frequently, a sample will be a "clinical sample," i.e., a sample derived from a patient. Such samples include, but are not limited to, bodily fluids which may or may not contain cells, e.g., blood (e.g., whole blood, serum or plasma), urine, sputum, saliva, sputum, tissue or fine needle biopsy samples, and archival samples with known diagnosis, treatment and/or outcome history. Biological samples may also include sections of tissues such as frozen sections taken for histological purposes. The sample also encompasses any material derived by processing a biological sample. Derived materials include, but are not limited to, cells (or their progeny) isolated from the sample, proteins or nucleic acid molecules extracted from the sample. Processing of a biological sample may involve one or more of: filtration, distillation, extraction, concentration, inactivation of interfering components, addition of reagents, and the like.

A "biomarker", as used herein, refers to a moiety or substance that is a distinctive indicator of a biological process, biological event and/or pathologic condition. For example, an antibody may be a biomarker for a disease (for example, an autoimmune disease or disorder such as Crohn's disease).

As used herein, the term "diagnosis" refers to the determination of the presence of a disease or disorder. In some embodiments of the present invention, methods for making a diagnosis are provided which permit determination of the presence of a particular disease or disorder.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Instructional material," as that term is used herein, includes a publication, a recording, a diagram, or any other medium of expression which can be used to communicate the usefulness of the nucleic acid, peptide, and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains one or more components of the invention or be shipped together with a container that contains the one or more components of the invention. Alternatively, the instructional material may be shipped separately from the container with the intention that the recipient uses the instructional material and the components cooperatively.

As used herein, an "immunoassay" refers to any binding assay that includes an antibody capable of binding specifically to a target molecule. The assay may be designed to detect and/or quantify the target molecule, for example a sandwich enzyme-linked immunosorbent assay (ELISA), or it may be designed to detect and/or quantify antibodies specific for a target molecule, for example an indirect ELISA.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

As used herein, the terms "measuring" or "measurement," or alternatively "detecting" or "detection," mean assessing the presence, absence, quantity or amount (which can be an effective amount) of a given moiety or substance within a sample, including the derivation of qualitative or quantitative concentration levels of such moiety or substance, or otherwise evaluating the values or categorization of a subject's clinical parameters.

As used herein, the terms "normal", "healthy", and "control" are used interchangeably. They include an individual or group of individuals who have not been diagnosed with a disease or disorder of interest (for example, an autoimmune disease or disorder). The terms are also used herein to describe a sample (e.g., a biological sample such as plasma) obtained from a normal, healthy or control individual.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogeneous or homogeneous in composition and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the term "polymerase chain reaction" ("PCR") refers to the method of K. B. Mullis (U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured, and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". As used herein, the terms "PCR product," "PCR fragment", "amplification product" or "amplicon" refer to the resultant mixture of compounds after two or more cycles of the PCR steps of denaturation, annealing and extension are complete. These terms encompass the case where there has been amplification of one or more segments of one or more target sequences.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or any combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

The terms "specifically binds" or "specific for" as used herein with respect to an antibody, refers to an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody A "therapeutic" treatment is a treatment administered to a subject who exhibits signs or symptoms of a disease or disorder, for the purpose of diminishing or eliminating those signs or symptoms.

As used herein, "treating a disease or disorder" means reducing the severity and/or frequency with which a sign or symptom of the disease or disorder is experienced by a patient.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, "sensitivity" refers to the ability to correctly identify a particular marker or pathological state when it is present (true positive rate). "Specificity", as used herein, refers to the ability to correctly exclude a particular marker or pathological state when it is not present (true negative rate). "Analytical sensitivity" or "analytical specificity", as used herein, is the ability to detect the presence or absence, respectively, of an infectious agent in a subject, while "clinical sensitivity" or "clinical specificity", as used herein, is the ability to positively or negatively diagnose, respectively, a disease or disorder in a subject.

DESCRIPTION

The present invention generally relates to kits, systems and methods for detecting MAP infection and/or diagnosing autoimmune diseases or disorders in patients. The present invention also relates to methods for determining when a patient presenting with a detectable MAP infection should be treated with anti-MAP therapy.

Biomarkers

In various embodiments, the present invention generally relates to kits and/or methods for detecting or measuring one or more biomarker in a biological sample.

In various embodiments, said biomarker of the present invention is measured in a biological sample. The biological sample can be a sample from any source which contains a polypeptide or a nucleic acid, such as a fluid, tissue, cell, cellular component, or a combination thereof. A biological sample can be obtained by appropriate methods, such as, by way of examples, blood draw, fluid draw, or biopsy. A biological sample can be used as the test sample; alternatively, a biological sample can be processed to enhance access to the polypeptides or nucleic acids, or copies of the nucleic acids, and the processed biological sample can then be used as the test sample.

In one embodiment, one or more of said biomarker of the present invention is one or more antibody. In one embodiment, one or more of said antibody is specific for MAP. In one embodiment, one or more of said antibody is not specific for MAP. In one embodiment, one or more of said antibody comprises an antibody specific for heat shock protein 65

(anti-Hsp65). In one embodiment, one or more of said antibody comprises an antibody specific for protein kinase G (anti-PknG). In one embodiment, one or more of said antibody comprises an antibody specific for MAP lipopentapetide (anti-L5P).

The methods described herein allow for specific detection of antibodies at low concentrations in a fluid sample. Detection may be achieved at antibody concentrations down to about 50, 40, 30, 20, 10, 5, or even 0.5 ng/ml, such as concentrations less than about 1000, 750, 500, 400, 300, 200, 100, 75, 50, 40, 30, 20, 10, 5 or even 0.5 ng/ml.

The methods described herein relating to detection of antibodies are particularly relevant to diagnostic and/or prognostic assays as relates to treatment and prevention of diseases or disorders, such as autoimmune diseases or disorders. Many diagnostic, prognostic and/or monitoring assays rely on detection of a biological marker of a particular disease state or disease susceptibility. Such biological markers are commonly proteins or polypeptides that are characteristic of a particular disease or associated with susceptibility to disease.

Detection of specific antibodies may be used diagnostically or prognostically to assess the disease state or other factors, such as disease progression. Antibodies typically serve as biological markers of infection, disease or disease susceptibility. For example, antibodies specific for a MAP antigen are indicative of a MAP infection. MAP infection has been implicated as causally related to many autoimmune diseases, such as Crohn's disease and ulcerative colitis. However, it should be noted that MAP infection alone does not necessarily predict the risk of developing symptomatic disease. Therefore, as is contemplated herein, additional biomarkers correlated specifically with autoimmune diseases or disorders, including antibodies, are required for rapid and accurate diagnosis.

In one embodiment, one or more of said biomarker of the present invention is one or more protein. In one embodiment, one or more of said protein is antigenic to the host and induces an immune response. In one embodiment, said immune response comprises antibodies specific for said one or more protein.

In one embodiment, one or more of said biomarker of the present invention is one or more nucleic acid. In one embodiment, said nucleic acid encodes a protein that is antigenic to the host and induces an immune response. In one embodiment, said immune response comprises antibodies specific for said one or more protein.

Assays

In various embodiments, the present invention generally relates to kits and/or methods comprising one or more assay to detect or measure one or more biomarker in a biological sample. In some embodiments, the present invention relates to kits and/or methods comprising one or more assay to determine whether said one or more biomarker is differentially expressed in said biological sample.

Biomarkers generally can be measured and detected through a variety of assays, methods and detection systems known to one of skill in the art. Various methods include but are not limited to immunoassays, microarray, PCR, RT-PCR, refractive index spectroscopy (RI), ultra-violet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/2004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

In various embodiments, to determine whether the level of expression of one or more biomarkers is increased or reduced in a biological sample of the subject, the level of expression of the at least one biomarker is compared with the level of at least one comparator control, such as a positive control, a negative control, a historical control, a historical norm, or the level of another reference molecule in the biological sample. The results of the diagnostic assay can be used alone, or in combination with other information from the subject, or other information from the biological sample obtained from the subject.

In various embodiments of the assays of the invention, the level of expression of the biomarker is determined to be elevated or increased when the level of expression of the biomarker is increased by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared with a comparator control.

In various embodiments of the methods of the invention, the level of expression of the biomarker is determined to be elevated or increased when the level of expression of the biomarker in the biological sample is increased by at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 25.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 20 fold, at least 25 fold, at least 30 fold, at least 40 fold, at least 50 fold, at least 75 fold, at least 100 fold, at least 200 fold, at least 250 fold, at least 500 fold, or at least 1000 fold, when compared with a comparator.

Different types of biomarkers and their measurements can be combined in the compositions and methods of the present invention. In various embodiments, one or more antibody is the biomarker. In other embodiments, one or more protein is the biomarker. In one embodiment, one or more of said protein is antigenic and induces the production of antibodies. In various embodiments, one or more nucleic acid is the biomarker. In one embodiment, said nucleic acid encodes one or more antigenic protein that induces antibodies.

In one embodiment, said biomarker of the present invention is an antibody. In one embodiment, said antibody is detected by measuring the formation of an antibody-antigen complex. To facilitate detection of the antibody-antigen complex, an appropriate detectable label may be utilized. There are many different labels and methods of labeling known to those of ordinary skill in the art. Examples of the types of labels which may be used in the present invention include enzymes, radioisotopes, fluorescent compounds, colloidal metals, chemiluminescent compounds, phosphorescent compounds, and bioluminescent compounds. Those of ordinary skill in the art will know of suitable labels, or will be able to ascertain such, using routine experimentation. The labeling moiety will be observable in conventional immunohistochemical detection techniques being, for example, a fluorescent dye such as fluorescein, a chemiluminescent reagent, a radioisotope, a colloidal label, such as colloidal gold or colored latex beads, an enzyme label, or any other known labeling complex.

By way of example, if the label on the antibodies against antibodies participates in a chemical reaction, then the product of that reaction may be quantified to quantify binding. For instance, the label may induce a color change that can be quantified with a spectrometer. The reference in such an instance may be absorption of light of a particular wavelength. The reference may also be a color chip or color scale. Further, if label is luminescent, binding can be quantified by measuring the intensity of light at a particular wavelength with a spectrometer. In such a case, the reference value may be an intensity value. Additionally, binding may be quantified by observing the interaction between labels on the antibodies specific for antibodies and labels bound to the antigens bound to the various surface areas. For example, if the label on the antibodies specific for antibodies comprises a fluorophore and the antigen bound to surface has a fluorophore bound to it, then transfer of energy between the fluorophores following exposure to light may be quantified. Energy may be transferred between the fluorophores by exposing the antibody-antibody-antigen complex to a wavelength and intensity of light sufficient to excite one of the fluorophores. When the other fluorophore is sufficiently close, energy may be transferred from the excited fluorophore to the other fluorophore, thereby causing the other fluorophore to emit light at a different wavelength than that used to stimulate the initial fluorophore. The intensity of light at the emitted wavelength may then be quantified using various devices, such as a spectrometer, to thereby quantify binding between antibodies within the sample and the antigen within the solution.

As is known in the art, detectable labels may be used to tag any member of the antibody-antigen complex, either directly (e.g., direct binding) or indirectly (e.g., secondary antibody) to facilitate detection. Various methods are known in the art to detect binding of the antigen with the antibody via a suitable detectable label. Detection may be by any method known in the art, such as immunologic techniques including immunoassays and the like. For example, detection of the antibody-antigen complex may be determined by techniques such as, but not limited to, Western blot analysis, flow cytometry, enzyme-linked immunosorbent assay (ELISA), radioimmunoassay (RIA), competition immunoassay, dual antibody sandwich assay, chemiluminescent assay, bioluminescent assay, fluorescent assay, and agglutination assay.

In one embodiment, said assay of the present invention comprises a diagnostic device. In one embodiment, said diagnostic device comprises: a first surface area; a protein or an antigenic fragment of said protein, wherein said protein or said antigenic fragment of said protein is bound to the first surface area; and a solution comprising labeled antibodies against said antibody specific for said protein. In one embodiment, said immunoassay of the present invention comprises an indirect ELISA. In one embodiment, said antibody to be detected by said immunoassay includes, but is not limited to, Hsp65, PknG, and L5P.

In one embodiment of the invention, one or more biomarker is a protein or polypeptide. Methods of measuring protein/polypeptide levels in a biological sample obtained from a subject include, but are not limited to, an immunochromatography assay, an immunodot assay, a Luminex assay, an ELISA assay, an ELISPOT assay, a protein microarray assay, a ligand-receptor binding assay, displacement of a ligand from a receptor assay, displacement of a ligand from a shared receptor assay, an immunostaining assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

In one embodiment of the invention, one or more biomarker is a nucleic acid. Methods for detecting a nucleic acid (e.g., mRNA), such as RT-PCR, real time PCR, microarray, branch DNA, NASBA and others, are well known in the art. Using sequence information provided by the database entries for the biomarker sequences, expression of the biomarker sequences can be detected (if present) and measured using techniques well known to one of ordinary skill in the art. For example, sequences in sequence database entries or sequences disclosed herein can be used to construct probes for detecting biomarker RNA sequences in, e.g., Northern blot hybridization analyses or methods which specifically, and preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

In some embodiments, quantitative hybridization methods, such as Southern analysis, Northern analysis, or in situ hybridizations, can be used (see Current Protocols in Molecular Biology, Ausubel, F. et al., eds., John Wiley &

Sons, including all supplements). A "nucleic acid probe," as used herein, can be a DNA probe or an RNA probe. The probe can be, for example, a gene, a gene fragment (e.g., one or more exons), a vector comprising the gene, a probe or primer, etc. For representative examples of use of nucleic acid probes, see, for example, U.S. Pat. Nos. 5,288,611 and 4,851,330. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target mRNA or cDNA. The hybridization sample is maintained under conditions which are sufficient to allow specific hybridization of the nucleic acid probe to mRNA or cDNA. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe having a mRNA or cDNA in the test sample, the level of the mRNA or cDNA in the sample can be assessed. More than one nucleic acid probe can also be used concurrently in this method. Specific hybridization of any one of the nucleic acid probes is indicative of the presence of the mRNA or cDNA of interest, as described herein.

Alternatively, a peptide nucleic acid (PNA) probe can be used instead of a nucleic acid probe in the quantitative hybridization methods described herein. PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a target nucleic acid sequence. Hybridization of the PNA probe to a nucleic acid sequence is used to determine the level of the target nucleic acid in the biological sample.

In another embodiment, arrays of oligonucleotide probes that are complementary to target nucleic acid sequences in the biological sample obtained from a subject can be used to determine the level of one or more biomarkers in the biological sample obtained from a subject. The array of oligonucleotide probes can be used to determine the level of one or more biomarkers alone, or the level of the one or more biomarkers in relation to the level of one or more other nucleic acids in the biological sample. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a nucleic acid of interest is hybridized with the array and its level is quantified. Hybridization and quantification are generally carried out by methods described herein and also in, e.g., published PCT Application Nos. WO 92/10092 and WO 95/11995, and U.S. Pat. No. 5,424,186. In brief, a target nucleic acid sequence is amplified by well-known amplification techniques, e.g., PCR. Typically, this involves the use of primer sequences that are complementary to the target nucleic acid. Asymmetric PCR techniques may also be used. Amplified target, generally incorporating a label, is then hybridized with the array under appropriate conditions. Upon completion of hybridization and washing of the array, the array is scanned to determine the quantity of hybridized nucleic acid. The hybridization data obtained from the scan is typically in the form of fluorescence intensities as a function of quantity, or relative quantity, of the target nucleic acid in the biological sample. The target nucleic acid can be hybridized to the array in combination with one or more comparators (e.g., positive control, negative control, quantity control, etc.) to improve quantification of the target nucleic acid in the sample.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}P$, $^{33}P$, $^{35}S$ or $^{3}H$. The nonradioactive entities are selected from ligands such as biotin, avidin, streptavidin or digoxigenin, haptenes, dyes, and luminescent agents such as radioluminescent, chemiluminescent, bioluminescent, fluorescent or phosphorescent agents.

Nucleic acids can be obtained from the cells using known techniques. Nucleic acid herein refers to RNA, including mRNA, and DNA, including cDNA. The nucleic acid can be double-stranded or single-stranded (i.e., a sense or an antisense single strand) and can be complementary to a nucleic acid encoding a polypeptide. The nucleic acid content may also be an RNA or DNA extraction performed on a biological sample, including a biological fluid and fresh or fixed tissue sample.

There are many methods known in the art for the detection and quantification of specific nucleic acid sequences and new methods are continually reported. A great majority of the known specific nucleic acid detection and quantification methods utilize nucleic acid probes in specific hybridization reactions. Preferably, the detection of hybridization to the duplex form is a Southern blot technique. In the Southern blot technique, a nucleic acid sample is separated in an agarose gel based on size (molecular weight) and affixed to a membrane, denatured, and exposed to (admixed with) the labeled nucleic acid probe under hybridizing conditions. If the labeled nucleic acid probe forms a hybrid with the nucleic acid on the blot, the label is bound to the membrane.

In the Southern blot, the nucleic acid probe is preferably labeled with a tag. That tag can be a radioactive isotope, a fluorescent dye or the other well-known materials. Another type of process for the specific detection of nucleic acids in a biological sample known in the art are the hybridization methods as exemplified by U.S. Pat. Nos. 6,159,693 and 6,270,974, and related patents. To briefly summarize one of those methods, a nucleic acid probe of at least 10 nucleotides, preferably at least 15 nucleotides, more preferably at least 25 nucleotides, having a sequence complementary to a nucleic acid of interest is hybridized in a sample, subjected to depolymerizing conditions, and the sample is treated with an ATP/luciferase system, which will luminesce if the nucleic sequence is present. In quantitative Southern blotting, the level of the nucleic acid of interest can be compared with the level of a second nucleic acid of interest, and/or to one or more comparator nucleic acids (e.g., positive control, negative control, quantity control, etc.).

Many methods useful for the detection and quantification of nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed elsewhere herein. Most preferably the detection of the duplex is done using at least one primer directed to the nucleic acid of interest. In yet another embodiment of PCR, the detection of the hybridized duplex comprises electrophoretic gel separation followed by dye-based visualization.

Typical hybridization and washing stringency conditions depend in part on the size (i.e., number of nucleotides in length) of the oligonucleotide probe, the base composition and monovalent and divalent cation concentrations (Ausubel et al., 1994, eds Current Protocols in Molecular Biology).

In one embodiment, the process for determining the quantitative and qualitative profile of the nucleic acid of interest according to the present invention is characterized in that the amplifications are real-time amplifications performed using a labeled probe, preferably a labeled hydrolysis-probe, capable of specifically hybridizing in stringent conditions with a segment of the nucleic acid of interest. The labeled probe is capable of emitting a detectable signal every time each amplification cycle occurs, allowing the signal obtained for each cycle to be measured.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 65° C. to 75° C. Preferably, the Tm for any one of the hydrolysis-probes of the present invention is in the range of about 67° C. to about 70° C. Most preferably, the Tm applied for any one of the hydrolysis-probes of the present invention is about 67° C.

In one aspect, the invention includes a primer that is complementary to a nucleic acid of interest, and more particularly the primer includes 12 or more contiguous nucleotides substantially complementary to the nucleic acid of interest. Preferably, a primer featured in the invention includes a nucleotide sequence sufficiently complementary to hybridize to a nucleic acid sequence of about 12 to 25 nucleotides. More preferably, the primer differs by no more than 1, 2, or 3 nucleotides from the target flanking nucleotide sequence. In another aspect, the length of the primer can vary in length, preferably about 15 to 28 nucleotides in length (e.g., 16, 17, 18, 19, 20, 21, 22, 23, 24, 25, 26, or 27 nucleotides in length).

In one embodiment, said one or more assay of the present invention is a culture assay. In one embodiment, said culture assay is specifically adapted to culture MAP. It should be recognized by those in the art that any known (or yet to be developed) methods of cell culture capable of growing MAP from a biological sample, can be used with the methods of the present invention. In one embodiment, said culture assay is one or more selected from the group consisting of: a Pozzato culture assay, a TiKa culture assay, and a Mycobacteria Growth Indicator Tube (MGIT) culture assay.

In one embodiment, said one or more assay is a phage amplification assay. In one embodiment, said phage amplification assay is optimized for detection of MAP. It should be recognized by those in the art that any phage amplification assay known (or yet to be developed) capable of detecting MAP infection from a biological sample can be used with the methods of the present invention.

Kits

The present invention also pertains to kits useful in the methods of the invention. Such kits comprise various combinations of components useful in any of the methods described elsewhere herein, including for example, materials for quantitatively analyzing a biomarker of the invention (e.g., antibody, polypeptide and/or nucleic acid), materials for assessing the activity of a biomarker of the invention (e.g., antibody, polypeptide and/or nucleic acid), and instructional material. For example, in one embodiment, the kit comprises components useful for the quantification of a desired antibody in a biological sample. In a further embodiment, the kit comprises components useful for the assessment of the activity (e.g., binding activity, blocking activity, etc.) of a desired antibody in a biological sample.

In a further embodiment, the kit comprises the components of an assay for monitoring the effectiveness of a treatment administered to a subject in need thereof, containing instructional material and the components for determining whether the level of a biomarker of the invention in a biological sample obtained from the subject is modulated during or after administration of the treatment. In various embodiments, to determine whether the level of a biomarker of the invention is modulated in a biological sample obtained from the subject, the level of the biomarker is compared with the level of at least one comparator contained in the kit, such as a positive control, a negative control, a historical control, a historical norm, or the level of another reference molecule in the biological sample. In certain embodiments, the ratio of the biomarker and a reference molecule is determined to aid in the monitoring of the treatment.

Detection and Diagnosis

In various embodiments, the present invention provides kits and/or methods for diagnosing, assessing the prognosis of, or assessing the risk of developing a disease or disorder in a subject. In some embodiments, the present invention provides kits and/or methods relating to biomarkers that can be used for diagnosing, assessing the prognosis of, or assessing the risk of developing a disease or disorder associated with MAP infection. In other embodiments, the methods of the present invention relate to kits and/or methods for diagnosing a subject with one or more autoimmune disease or disorder.

In one embodiment, the method comprises detecting the level (e.g., antibody) of at least one biomarker in a biological sample obtained from the subject, comparing the level of the at least one biomarker in the biological sample to a comparator of the at least one biomarker; and determining that the subject is at increased risk of developing a disease or disorder when the at least one biomarker is differentially expressed in the biological sample as compared to the comparator. In one embodiment, said biomarker is positively or negatively correlated with MAP infection. In one embodiment, said biomarker is positively or negatively correlated with one or more autoimmune disease or disorder. In one embodiment, said biomarker includes one or more antibody. In one embodiment, said antibody includes, but is not limited to, anti-Hsp65, anti-PknG, and anti-L5P.

In some embodiments, one or more autoimmune disease or disorder is associated with MAP infection. In some embodiments, one or more autoimmune disease includes, but is not limited to, Crohn's Disease (CD), Ulcerative Colitis (UC), Irritable Bowel Syndrome (IBS), Multiple Sclerosis (MS), Type 1 Diabetes Mellitus (T1DM), Sjogren's Syndrome (SS), Systemic Lupus Erythematosus (SLE), Depression, Parkinson's Disease (PD), Alzheimer's Disease (AD), celiac disease, thyroiditis, rheumatoid arthritis, Blau syndrome, psoriasis, and Complex Regional Pain Syndrome (CRPS).

In various embodiments, the subject is a human subject, and may be of any race, sex and age. Representative subjects include those who are at risk of developing a MAP infection, those who are suspected of having a MAP infection, those who have been diagnosed with a MAP infection, those who have been diagnosed with one or more autoimmune disease associated with MAP infection.

In some embodiments, said diagnosing of said subject comprises determining whether the subject has a differentially expressed level of one or more biomarker. In some embodiments, at least two biomarkers are required to diagnose said subject. In some embodiments, at least three biomarkers are required to diagnose said subject. In some embodiments, at least one biomarker and at least one additional clinical assay is required to diagnose said subject. In some embodiments, at least two biomarkers and at least one additional clinical assay is required to diagnose said subject. In some embodiments, at least three biomarkers and at least one additional clinical assay is required to diagnose said subject.

In one embodiment, the method comprises using a multi-dimensional non-linear algorithm to determine if the level (e.g. antibodies) of a set of biomarkers in the biological sample is statistically different than the level in a comparator sample. In some embodiments, the algorithm is drawn from the group consisting essentially of: linear or nonlinear regression algorithms; linear or nonlinear classification algorithms; ANOVA; neural network algorithms; genetic algorithms; support vector machines algorithms; hierarchical analysis or clustering algorithms; hierarchical algorithms using decision trees; kernel based machine algorithms such as kernel partial least squares algorithms, kernel matching pursuit algorithms, kernel fisher discriminate analysis algorithms, or kernel principal components analysis algorithms; Bayesian probability function algorithms; Markov Blanket algorithms; a plurality of algorithms arranged in a committee network; and forward floating search or backward floating search algorithms.

In one embodiment, the method comprises detecting one or more markers in a biological sample of the subject. In some embodiments, the level of one or more of markers of the invention in the biological test sample of the subject is compared with the level of the biomarker in a comparator. Non-limiting examples of comparators include, but are not limited to, a negative control, a positive control, standard control, standard value, an expected normal background value of the subject, a historical normal background value of the subject, a reference standard, a reference level, an expected normal background value of a population that the subject is a member of, or a historical normal background value of a population that the subject is a member of. In one embodiment, the comparator is a level of the one or more biomarker in a sample obtained from a subject not having a disease or disorder, such as an autoimmune disease or disorder. In one embodiment, the comparator is a level of the one or more biomarker in a sample obtained from a subject known not to have a disease or disorder.

In various embodiments, the kits and/or methods of the present invention are able to detect a biomarker with at least 70%, 75%, 80%, 85%, 90%, 91%, 92%, 93%, 94%, 95%, 96%, 97%, 98%, 99%, 100% sensitivity; at least 70%, 75%, 80%, 85%, 90%, 91%, 92%, 93%, 94%, 95%, 96%, 97%, 98%, 99%, 100% specificity; and/or at least 70%, 75%, 80%, 85%, 90%, 91%, 92%, 93%, 94%, 95%, 96%, 97%, 98%, 99%, 100% accuracy.

In various embodiments, the kits and/or methods of the present invention are able to detect the presence of an infectious agent with at least 70%, 75%, 80%, 85%, 90%, 91%, 92%, 93%, 94%, 95%, 96%, 97%, 98%, 99%, 100% sensitivity; at least 70%, 75%, 80%, 85%, 90%, 91%, 92%, 93%, 94%, 95%, 96%, 97%, 98%, 99%, 100% specificity; and/or at least 70%, 75%, 80%, 85%, 90%, 91%, 92%, 93%, 94%, 95%, 96%, 97%, 98%, 99%, 100% accuracy.

In various embodiments, the kits and/or methods of the present invention are able to diagnose a disease or disorder with at least 70%, 75%, 80%, 85%, 90%, 91%, 92%, 93%, 94%, 95%, 96%, 97%, 98%, 99%, 100% sensitivity; at least 70%, 75%, 80%, 85%, 90%, 91%, 92%, 93%, 94%, 95%, 96%, 97%, 98%, 99%, 100% specificity; and/or at least 70%, 75%, 80%, 85%, 90%, 91%, 92%, 93%, 94%, 95%, 96%, 97%, 98%, 99%, 100% accuracy.

Treatment

In one embodiment, the present invention includes a method of detecting MAP infection in a subject. In one embodiment, the present invention provides a method of determining whether a subject with detectable MAP infection should be diagnosed with an autoimmune disease. In one embodiment, the methods of the present invention determine whether a subject diagnosed with an autoimmune disease should be treated with a therapeutic specific to MAP infection. In one embodiment, the methods of the present invention determine whether a subject diagnosed with an autoimmune disease should be treated with a therapeutic specific to said autoimmune disease. In one embodiment, said therapeutic is an antibiotic.

In one embodiment, the method comprises administering to the subject an effective amount of one or more therapeutic. In one embodiment, said therapeutic is an antibiotic. It should be recognized by those in the art that any antibiotic capable of treating a MAP infection can be used with the methods of the present invention. In some embodiments, one or more antibiotic includes, but is not limited to, Cefradine (cephradine), cefrotil, cefroxadine, cefsumide, ceftaroline, ceftazidime, cefteram, ceftezole, ceftibuten, ceftiofur, ceftiolene, ceftioxide, ceftizoxime, Ceftobiprole, ceftriaxone, cefuracetime, cefuroxime, cefuzonam, cephalosporin, chloramphenicol, cilastatin, ciprofloxacin, clarithromycin, clinafloxacin, clindamycin, clofazimine, cloxacillin, demeclocycline, dicloxacillin, dirithromycin, doripenem, doxycycline, enoxacin, ertapenem, erythromycin, flucloxacillin, flumequine, fluoroquinolone, gatifloxacin, gemifloxacin, gentamicin, grepafloxacin, imipenem, kanamycin, ketolide, levofloxacin, Lincomycin, linezolid, Linezolid, lomefloxacin, meropenem, metronidazole, mezlocillin, minocycline, moxifloxacin, mycobutin, nadifloxacin, nafcillin, nalidixic acid, neomycin, netilmicin, nitrofurantoin, norfloxacin, ofloxacin, oxacillin, oxolinic acid, oxytetracycline, paromomycin, pazufloxacin, pefloxacin, penicillin g, penicillin v, piperacillin, piromidic acid pipemidic acid, pivampicillin, pivmecillinam, primaxin, prulifloxacin, rifampin, rosoxacin, roxithromycin, rufloxacin, sitafloxacin, sparfloxacin, streptomycin, sulfamethizole, sulfamethoxazole, sulfisoxazole, Teicoplanin, Telavancin, telithromycin, temafloxacin, tetracycline, ticarcillin, tobramycin, tosufloxacin, trimethoprim-sulfamethoxazole, trovafloxacin, vancocin, vancomycin, and lipopeptide.

In other embodiments, one or more antibiotic may include, but is not limited to, Amoxicillin, Ampicillin, Cloxacillin, Dicloxacillin, Nafcillin, Oxacillin, Penicillin G, Penicillin V, Piperacillin, Cefadroxil (cefadroxyl), Cefalexin (cephalexin), Cefalotin (cephalothin), Cefapirin (cephapirin), Cefazolin (cephazolin), Cefradine (cephradine), Cefaclor, Cefotetan, Cefoxitin, Cefprozil (cefproxil), Cefuroxime, Cefdinir, Cefixime, Cefotaxime, Cefpodoxime, Ceftizoxime, Ceftriaxone, Ceftazidime, Cefepime, Ceftobiprole, Ceftaroline, Aztreonam, Imipenem, Imipenem, cilastatin, Doripenem, Meropenem, Ertapenem, Azithromycin, Erythromycin, Clarithromycin, Dirithromycin, Roxithromycin, Clindamycin, Lincomycin, Amikacin, Gentamicin, Tobramycin, Ciprofloxacin, Levofloxacin, Moxifloxacin, Trimethoprim-Sulfamethoxazole, Doxycycline, Tetracycline, Vancomycin, Teicoplanin, Telavancin, and Linezolid.

Administration of the therapeutic agent in accordance with the methods of the present invention may be continuous or intermittent, depending, for example, upon the recipient's physiological condition, whether the purpose of the administration is therapeutic or prophylactic, and other factors known to skilled practitioners. The administration of the agents or modified cell of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

One or more suitable unit dosage forms having the therapeutic agent(s), which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents to be used with the methods of the present invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations to be used with the methods of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The therapeutic agents can be formulated and administered by any conventional means available for use in conjunction with pharmaceuticals, either as individual therapeutic active ingredients or in a combination of therapeutic active ingredients. They can be administered alone but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the therapeutic agent may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition to be used with the methods of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the therapeutic can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Culture, Antibody and Phage Amplification Methods Variably Detect MAP In accordance with consensus recommendations from the MAP conference held at Temple University in March 2017, the study of the present Example was undertaken to examine alternative approaches able to detect, isolate and/or culture MAP from human blood samples (Kuenstner, J. T., et al., *Front Public Health,* 2017, 5: 208). The primary goals of the study were to assess the degree of viable culturable MAP bacteremia in a test human population, definite identification of the organisms cultured and to determine the relative predominance of MAP in CD patients compared to controls, which included several non-CD subjects with various autoimmune diseases. A secondary goal included parallel evaluation of two culture-based approaches developed in different laboratories (TiKa culture and Pozzato culture), a rapid phage amplification detection method and the existing MGIT culture method, and a series of MAP specific antibody tests developed at several other laboratories. Lastly to establish a degree of reliability in the results, selected subjects showing initial positive MAP detection were also followed up with a repeat test one year later.

The materials and methods of the present Example are now described herein.

Study Design and Participants

The study protocol was reviewed on Oct. 20, 2017 by the Temple University IRB (IRB protocol #24790). This case-control study included 201 subjects-61 patients with CD and 140 non-CD controls. The non-CD control group included 16 patients with UC and various other autoimmune diseases. The first 159 subjects in the study were recruited from the practice of a gastroenterologist in Winter Park, Florida, Dr. Ira Shafran. In addition, 42 of the subjects were recruited from the Human Paratuberculosis Foundation website (www.humanpara.org) and the phlebotomy of the second group was performed at a site in New York City. A single blood collection was performed on 192 subjects during May through August 2018. For 9 of the subjects a second blood sample was obtained in August 2019 to determine if they had a transient or persistent MAP infection. Selection of these subjects was based on an initial positive MAP culture or phage assay and for the availability to donate a second sample one year later in Philadelphia. One of these subjects had chronic thyroiditis and irritable bowel syndrome (IBS), three had chronic thyroiditis, four subjects were asymptomatic and healthy, and one had IBS.

Diagnosis and Diagnostic Categorization

The subjects completed a consent form and a questionnaire about their medical history and BCG status. The patients with CD or UC also completed an additional questionnaire during enrollment to assess the modified Harvey Bradshaw index (HBI). All subject information was kept confidential in accordance with standard medical practice.

Procedures

Blood samples were collected from all 201 participants at enrollment in EDTA blood collection tubes. Peripheral blood leukocytes (PBLs)/buffy coat specimens were prepared from the whole blood samples and then shipped by courier to each of the laboratories performing the cultures (Bull and Grant laboratories in London and Belfast, UK, respectively, and Naser laboratory in Florida, USA). The courier delivery time to the Bull and Grant laboratories was subject to inconsistently applied international customs regulations and thus ranged from 3 to 7 days while the courier delivery time to the Naser laboratory was one day. The plasma from the blood samples was collected and frozen at −80 C until serology testing was performed later. All samples were identified by a study number and the laboratory scientists were blinded to all clinical information, diagnoses, and personal identifiers.

MGIT Culture

Peripheral blood leukocytes (PBLs) from the EDTA buffy coats were inoculated into BACTEC MGIT ParaTB medium with supplements (OADC and mycobactin J as detailed above) and incubated for 6 months at 37 C. After incubation, the MGIT culture was centrifuged, DNA extracted from the pellet, and nested IS900 PCR was performed as described (Naser, S. A., et al., *Lancet,* 2004, 364: 1039-1044). Subcultures were made on all PCR-positive MGIT cultures to attempt recovery of MAP in pure culture.

TiKa Culture

Buffy coats transported in Middlebrook 7H9 transport media were centrifuged at 800×g for 10 min at RT and the pellet re-suspended in 10 ml freshly prepared TiKa-KiC (Bull, T. J., et al., *Front Microbiol,* 2016, 7: 2112) decontamination cocktail then incubated at 37° C. for 20-24 h with shaking (150 rpm). Samples were centrifuged at 2500×g for 15 min at RT, pellets re-suspended in 1 ml recovery medium (Pozzato culture) plus TiKa supplements A (1 μg/ml), M1, M2 and M3 (1 μl/ml)) and incubated 37° C. for 2 days. Samples were then added to MGIT culture tubes supplemented with PANTA plus Mycobactin J (2 μg/ml) and TiKa supplement A (1 μg/ml) and incubated at 37° C. for up to 4 months. Cultures showing visible growth were centrifuged at 2500×g for 10 min at RT and pellets subcultured on to solid Pozzato culture (1.5% agar) in 24 well plates then overlaid with semi-solid Pozzato culture 0.75% agar containing TiKa supplement A (1 μg/ml), sealed with gas permeable membrane and incubated at 37° C. in 5% CO2. MAP DNA was extracted from colonies as previously described (Bull, T. J., et al., *J Clin Microbiol,* 2003, 41: 2915-2923). Samples were deemed MAP positive if IS900 and F57 PCR positive biomass was obtained.

Pozzato Culture and Phage Amplification Assay

PBL samples were centrifuged (2500×g for 15 min) and resuspended in 1 ml Middlebrook 7H9 broth supplemented with 10% OADC (both Difco) and 2 mM $CaCl_2$) (Sigma). The phage amplification assay and Pozzato culture were performed as described previously (Swift, B. M., et al., *Virulence,* 2016, 7: 779-788; Pozzato, N., et al., *J Microbiol Methods,* 2011, 84: 413-417; Grant, I. R., et al., *J Dairy Sci,* 2017, 100: 9723-9735; Foddai, A., et al., *Appl Environ Microbiol,* 2009, 75: 3896-3902). Briefly, following a 15 min incubation at RT and a thorough vortex, 500 μl of each PBL sample was inoculated into a screw cap glass culture tube containing 4 ml modified 7H9 medium, PANTA antibiotic supplement, and mycobactin J, as described by Pozzato et al. (Pozzato, N., et al., *J Microbiol Methods,* 2011, 84: 413-417) but with no egg yolk added (referred to as 'Pozzato culture') (Grant, I. R., et al., *J Dairy Sci,* 2017, 100: 9723-9735). The second 500 μl of each PBL sample was subjected to the optimized phage amplification assay (Foddai, A., et al., *Appl Environ Microbiol,* 2009, 75: 3896-3902), which proceeded as follows: 108 D29 mycobacteriophages were added to each 1 ml test sample to infect any MAP cells present, and samples were incubated at 37 C. After 2 h, the extraneous seed phages were inactivated by treatment with virucide (final concentration 10 mM ferrous ammonium sulphate) for 10 min, and then the sample was diluted with 5 ml 7H9/OADC/$CaCl_2$) (2 mM) broth. Incubation of samples proceeded until a total of 3.5 h had elapsed since addition of phages, at which point the entire sample was plated with *Mycobacterium smegmatis* $mc^2$ 155 sensor cells and 5 ml molten Middlebrook 7H9 agar in Petri dishes. Once solidified, agar plates were incubated overnight at 37 C and examined next day for evidence of zones of clearing ('plaques'), the presence of which would be indicative of the viable mycobacteria in the sample, A PML sample was deemed MAP culture positive if IS900 and F57 PCR positive biomass (broth pellet or colony on Herrold's egg yolk-mycobactin J (HEYM) was obtained.

MAP Antibody Assay

Plasma samples for each patient were assayed using the IDEXX *Mycobacterium paratuberculosis* antibody test kit for detection of antibody to MAP in bovine serum, plasma and milk. This kit was adapted for human use as described previously (Bernstein, C. N., et al., *J Clin Microbiol,* 2004, 42: 1129-1135). Human plasma controls optical density (OD) values were used to calculate sample/positive (S/P) ratios and interpret the assay.

PtpA and PknG ELISA Test

The antibodies against virulence factors secreted by MAP during infections were measured in plasma specimens as described previously (Bach, H., et al., *Scand J Gastroenterol,* 2011, 46: 30-39; Bach, H., et al., *Biomed Res Int,* 2018, 2018: 1450828). These antigens included the protein tyrosine phosphatase (PtpA) and the protein kinase G (PknG) (Bach, H., et al., *Biomed Res Int,* 2018, 2018: 1450828; Bach, H., et al., *Cell Host Microbe,* 2008, 3: 316-322). Recombinant PtpA and PknG were produced in *M. smegmatis* and according to published procedures (Bach, H., et al., *Biomed Res Int,* 2018, 2018: 1450828; Bach, H., et al., *Cell Host Microbe,* 2008, 3: 316-322).

Hsp65 Antibody Assay

Hsp65 antibody from the blood was measured by direct ELISA assays described previously (Zhang, P., et al., *Microorganisms,* 2019, 8). Recombinant Hsp65 from *Mycobacterium avium* subspecies hominissuis (MAH) was produced at GenScript Corp (genscript(dot)com) through contract work and used to coat the 96-well plate.

Whole Genome Sequencing (WGS)

One MAP isolate from a single subject, primarily isolated using TiKa culture was whole genome sequenced. Briefly, three colonies were collected from Pozzato semi-solid culture washed once in TE xl buffer (Tris HCl-EDTA pH8, Sigma, UK), killed by heating at 98° C. for 30 mins in TE xl, then gDNA extracted using the QiaPrep DNA kit (Qiagen, UK) according to manufacturer's instructions. Whole genome sequencing was as previously described (Witney, A. A., et al., *BMC Med,* 2016, 14: 46). DNA concentration and integrity were determined using Qubit High Sensitivity DNA assay (Life Technologies, UK) and Agilent Tape station 2100 using a genomic screentape respectively. Library preparation and sample indexing was undertaken using NexteraXT DNA according to the manufacturer's instructions followed by bead-based normalisation and pooling with other libraries being sequenced. Sequencing was performed using Illumina v3 chemistry using 2×300 bp paired-end reads and sequenced on an Illumina MiSeq Sequence reads were mapped to the MAP reference genome (RefSeq accession: NC_002944.2) using bwa mem v0.7.3a-r367 (Li, H., arXiv, 2013, 1303.3997v2 [q-bio.GN]), alignments were sorted, duplicates were removed with samtools v0.1.19 (Li, H., et al., *Bioinformatics,* 2009, 25: 2078-2079) and site statistics generated using samtools mpileup. The compiled genome was mapped against other mycobacteria using NCBI Sequence Viewer (Version 3.36.0, NCBI, USA) and Snapgene (Version 4.3.11, GSL Biotech, USA).

Data Analyses and Statistical Methods

Data were expressed as frequencies and percentages for categorical variables and mean±standard deviation (SD) and/or median (range or quartile range) for continuous variables. Associations between potential risk factors or assay methods of interest and select disease status (i.e., CD or CD+UC) were evaluated using the Fisher's exact test for two groups and Wald test for a continuous variable. Multivariable logistic regression analyses were performed on the select diseases to explore their association with or predictability of the disease using different assay methods (culture, antibodies or both) when other potential risk factors or confounding variables such as age and gender are adjusted in the regression model. To define a cutoff value of a continuous covariate or an assay variable for inclusion in a logistic regression model in predicting a patient's outcome, the cutoff was chosen to achieve an optimal classification criterion based on the Euclidean distance method. Both the continuous and dichotomized versions of continuous variables were included in the logistic regression model as candidate variables in a stepwise variable selection procedure. A stay probability of 0.10 and entry probability of 0.25 were employed to arrive at a final regression model. Therefore, variables with non-significant predictive abilities for a disease state were dropped from the multivariable logistic regression model to keep the model parsimonious. Age and sex were included in all regression models a priori. Both raw and adjusted odds ratios of having CD or CD+UC and their 95% confidence intervals (CIs) were reported whenever appropriate. P-values less than 0.05 were considered statistically significant. SAS version 9.4 (SAS Institute Inc., Cary, NC, USA) was used for all the data analyses.

The results of the present Example are now described herein.

The subject demographic data by subgroups for the study appears in FIG. 1. The median patient age and age ranges are presented in addition to the mean age and standard deviation because the data is asymmetric, and this approach is favored for asymmetric distributions such as age data. In the study, the non-CD patients appeared to be slightly older than the CD patients (median: 57.5 vs. 47 years old) and have a similar gender composition (59% vs. 54% females).

The analytical sensitivities (the ability of the method to detect the organism, rather than clinical sensitivity, which is the ability of the test to detect disease) of the culture methods for viable MAP bacteremia in order of the highest to lowest are: 1) Pozzato culture (124/201 or 62% of all subjects, 35/61 or 57% of CD patients), 2) Phage assay (113/201 or 56% of all subjects, 28/61 or 46% of CD patients), 3) TiKa culture (64/201 or 32% of all subjects, 22/61 or 36% of CD patients) and 4) MGIT culture (36/201 or 18% of all subjects, 15/61 or 25% of CD patients). These results are summarized in FIG. 2. Results are reported as number and % of subjects in each category, with subject numbers in parentheses for CD and UC only patients. The single asterisk (*) indicates that two CD patients also had diagnosis of UC. Double asterisks (**) indicate that the Non-CD category includes the 14 UC only subjects. The dagger (†) indicates that two subjects had missing TiKa culture results.

Figure 4:
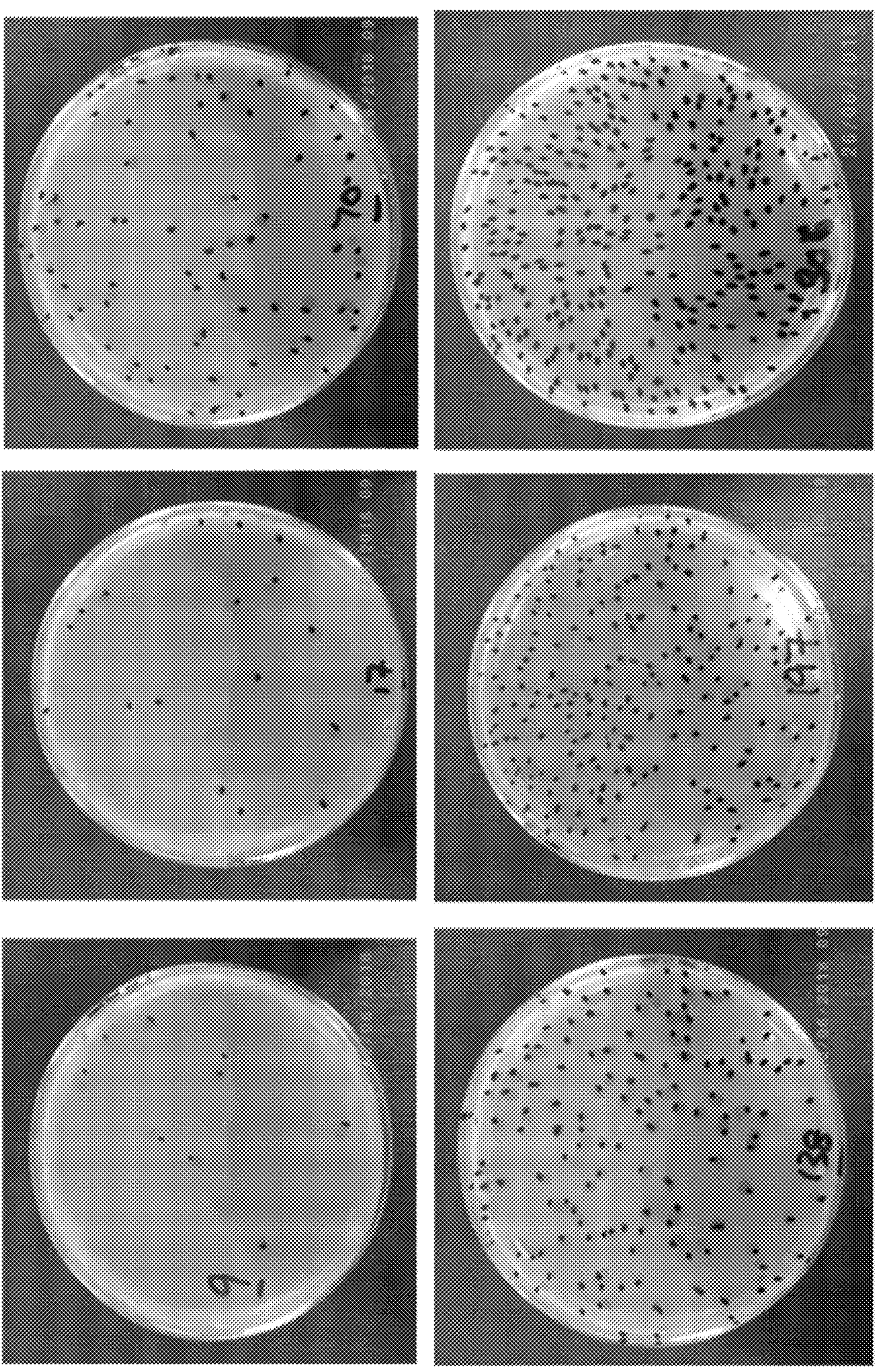
FIG. 4 depicts exemplary plates showing plaque numbers observed in phage assay positive PBL samples tested during June 2018. Overall, plaque numbers ranged from 1-500/half PBL sample (other half of sample was cultured in Pozzato broth).
Figure 5:
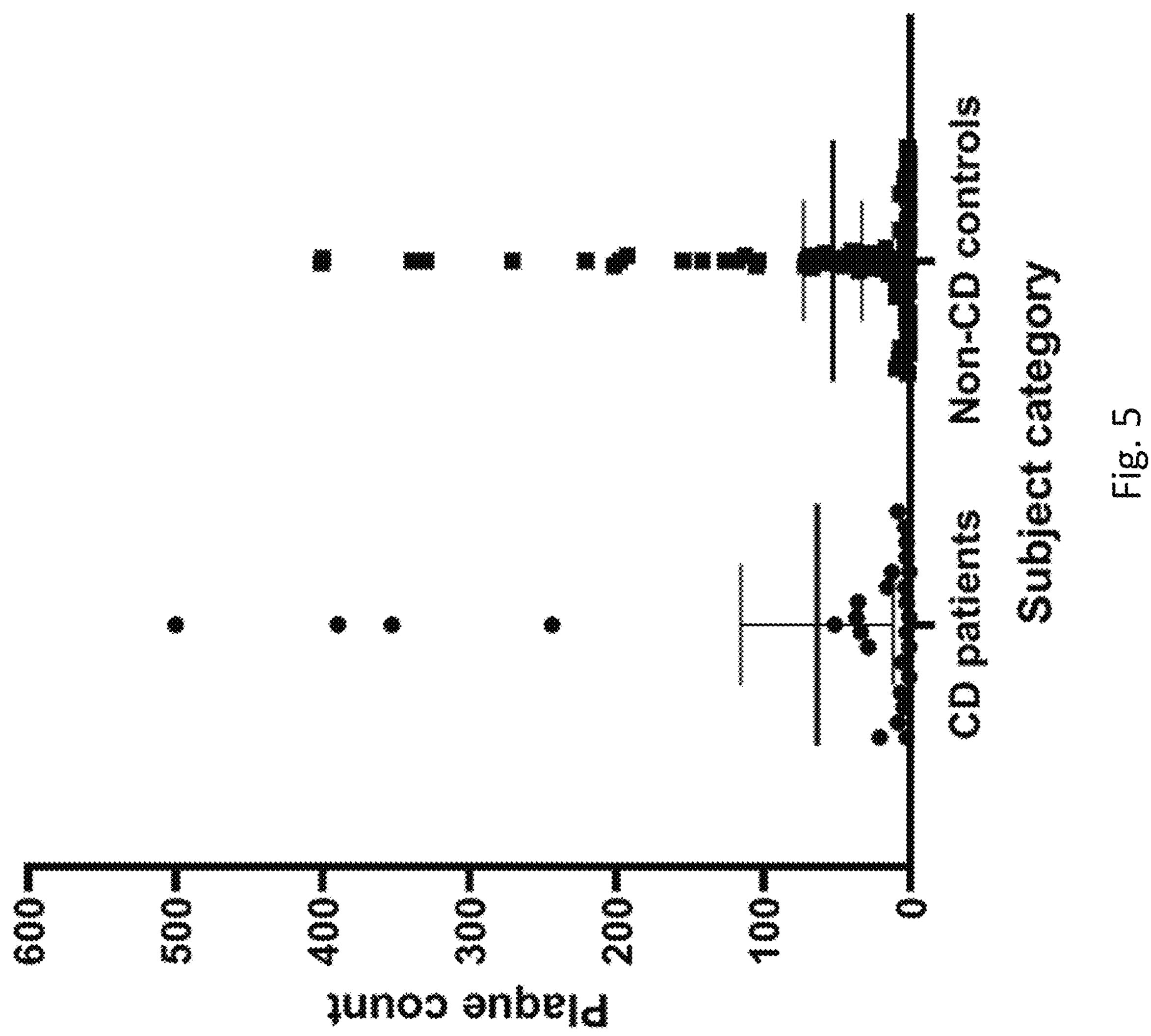
FIG. 5 depicts the mean plaque numbers ±95% CI (or SEM) obtained for phage assay positive PBLs from CD patients and non-CD controls. A T-test indicated no significant difference between mean plaque numbers of the two subject categories (CD patients 63.85 plaques and Non-CD controls 53.27 plaques, p-value=0.6385), but variance within the two subject categories is significantly different (p-value=0.0091).

Interrelationships between results of the three liquid culture methods (MGIT, TiKa and Pozzato) are illustrated in FIG. 3. The asterisk (*) indicates that there were two samples with "contaminated" results from the Bull lab. Additional data show numbers of plaques observed in CD patients and non-CD control (FIG. 4 and FIG. 5).

Figure 7:
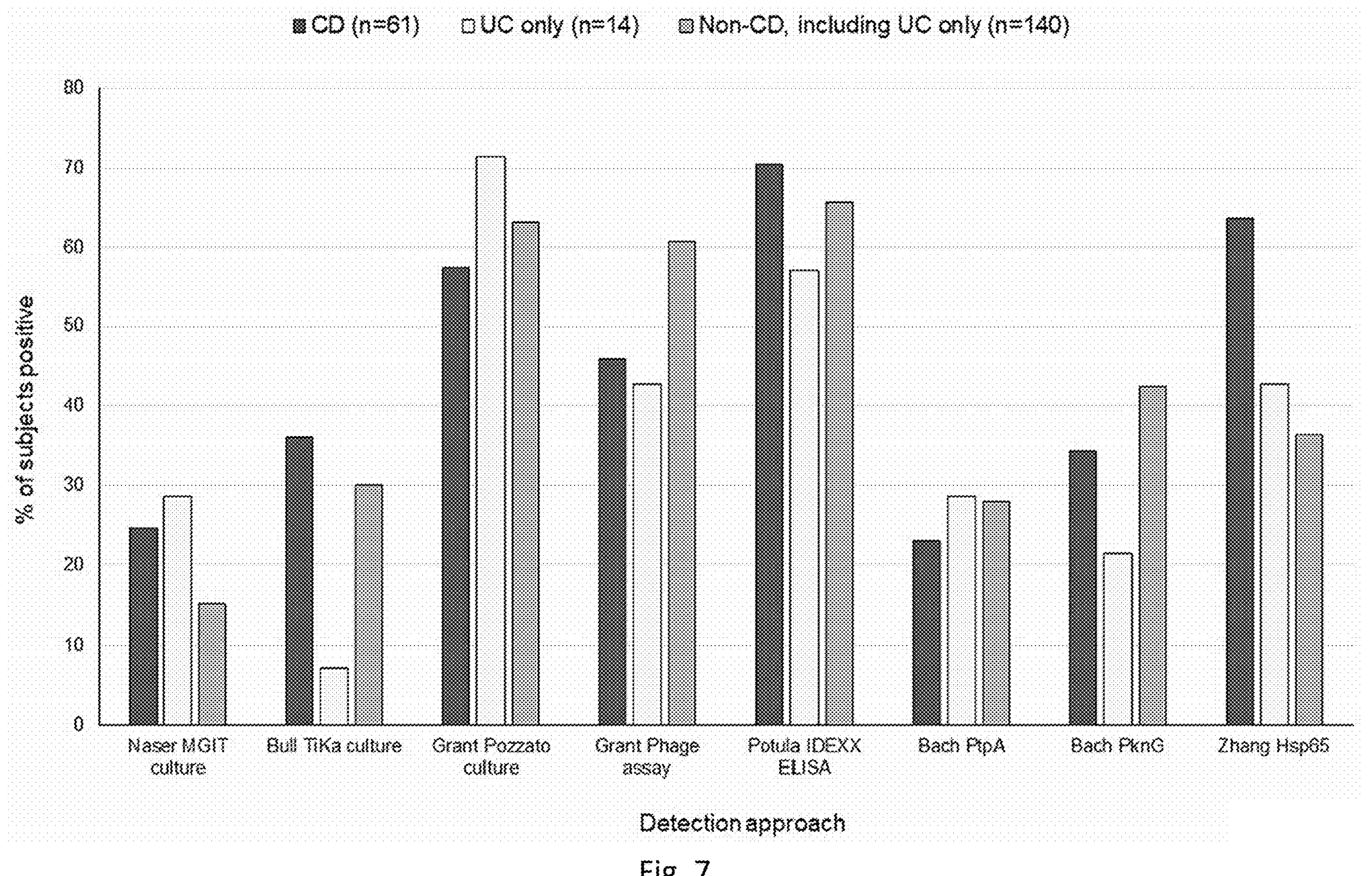
FIG. 7 depicts exemplary results demonstrating the comparison of the percentages of subjects showing evidence of MAP detected by all cultural and serological methods employed; separately for CD patients, UC only patients and Non-CD controls (including 14 UC only patients).

FIG. 6 depicts the association of clinically diagnosed CD patients with various categorical variables of interest. Of note, the younger age group (≤52 years old) seemed to be more likely to have CD when compared to the older age group (>52 years old) (OR (95% CI): 2.66 (1.42, 4.99); p=0.003). Among all assay methods, a negative Hsp65 antibody assay <0.74 appeared to differentiate CD from non-CD cases (p=0.06 and 0.02, see Table 3). FIG. 7 shows the comparison of MAP detected by all cultural and serological methods among the subjects.

To investigate the independent relationships of the culture and the serologic methods with the presence of MAP and the clinical diagnosis in subjects i.e., CD or CD+UC vs. (non-CD or non-CD nor UC), a multivariable logistic regression model was used for association analyses. The significant findings regarding associations with MAP culture and/or antibody data are provided using the odds ratio (OR) and its 95% confidence interval (CI) for having CD or having either CD or UC and a p-value. The OR data for all culture methods is presented adjusted for age and gender in FIG. 8, which is more robust than the unadjusted/marginal odds ratio data that is included in FIG. 6. Results are reported from six (6) logistic regression models (3 assay method variables inclusion settings×2 select diseases (CD or CD+UC), all adjusted for age (≤52 vs. >52) and gender. NS indicates not significant and the double dagger (‡) indicates the OR and 95% CI for a 0.2-unit increment of Hsp65 antibody.

The associated p-value was 0.037 with an OR (95% CI) of 2.36 (1.06, 5.28) for the MGIT culture for MAP positivity corresponding to CD patients and this associated p-value supports the predictive power of this culture method. This was also true when UC subjects were included along with the CD subjects in the analysis and the result of this analysis was a p-value of 0.006 and adjusted OR (95% CI) of 3.19 (1.40, 7.23) for having CD+UC when comparing MGIT culture positive to negative subjects.

The TiKa culture showed a significant association (data not included) for positive MAP cultures, but the TiKa, Phage assay and Pozzato culture methods did not reach the statistical significance at 0.10. Therefore, the preceding methods did not make the final model predicting the presence of CD in our study. Nonetheless, the Phage assay and Pozzato culture methods detected a higher proportion of MAP infections in non-CD/UC cohort while TiKa culture had a reverse trend similar to the one exhibited by the MGIT culture method (see FIG. 2).

Amongst the several serology tests, the highest and only significant correlation to the presence of CD occurred with the Hsp65 antibody. At a cutoff value of 0.74, this method had the best ability to discriminate between CD patients and non-CD subjects (adjusted OR (95% CI) of having CD comparing Hsp65 Ab>0.74 vs. Hsp65 Ab≤0.74: 2.40 (1.25, 4.61); p-value 0.009; FIG. 8). The PknG antibody also had a significant negative correlation to the presence of CD/UC in our patients as compared to the non-CD/UC subjects (adjusted OR (95% CI) of having CD/UC comparing PknG negatives to positives: 2.18 (1.12, 4.23); p-value: 0.022. Spearman correlation showed that the Hsp65 antibody had a weak correlation with the HBI (Spearman coefficient=0.28, p=0.03) and the Phage Plaque counts showed a very weak correlation with the HBI (Spearman coefficient=0.12, p=0.37) among 60 CD patients who had such data. It is worth noting that the range of the HBI in the study population was limited and few patients had an HBI greater than 5.

The MGIT culture and the Hsp65 antibody assay were the best discriminators between the CD patients and the non-CD subjects for the study population, both each in its individual own (culture or antibody) category and together independently in the culture and antibody combined set, after having adjusted for age and sex (and each other in the latter case) (see FIG. 8). If we combine all three culture methods into one category, i.e., culture is positive if any one of the three cultures methods are positive and negative if otherwise, then the overall agreement between this category and Phage assay achieved a rate of 75% with an exact 95% CI of (68%, 80%). The kappa statistic (SE) for agreement between the two diagnostic methods was 0.26 (0.08) with a 95% CI of (0.11, 0.42), showing the strength of agreement as fair (FIG. 9).

Viable MAP bacteremia was also detected in patients with autoimmune conditions who did not have either CD or UC: 1) Pozzato culture (33/57 or 58%), 2) Phage assay (36/57 or 63%), 3) TiKa culture (19/56 or 34%) and 4) MGIT culture (9/57 or 16%). All 9 subjects who had an initial positive MAP culture or Phage assay were positive on the second Phage assay from a second blood sample obtained one year later.

Figure 10:
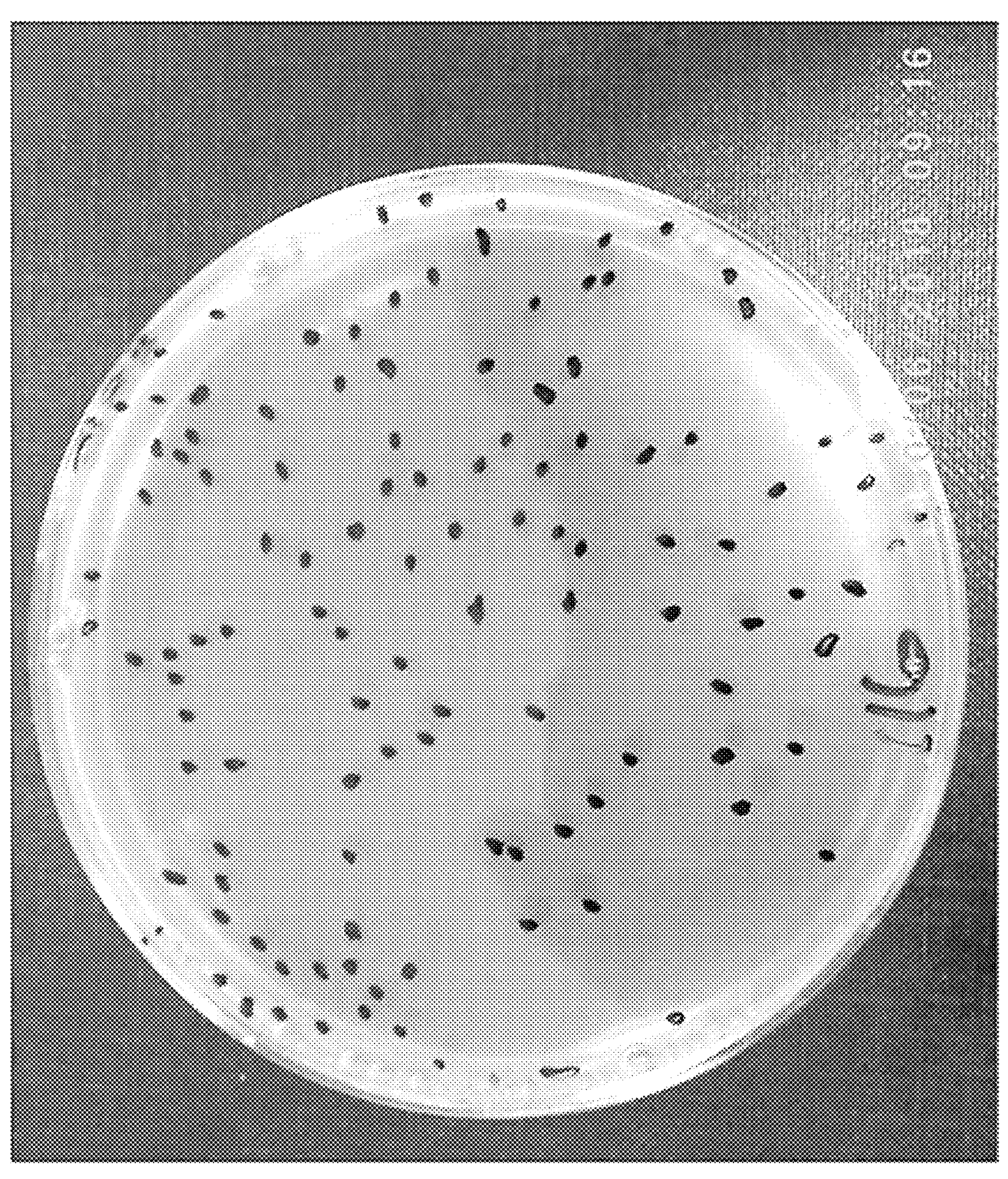
FIG. 10 depicts a representative image of Phage isolate recovered from the blood of a single subject with IBS was confirmed as MAP by whole genome sequencing (WGS).
Figure 11:
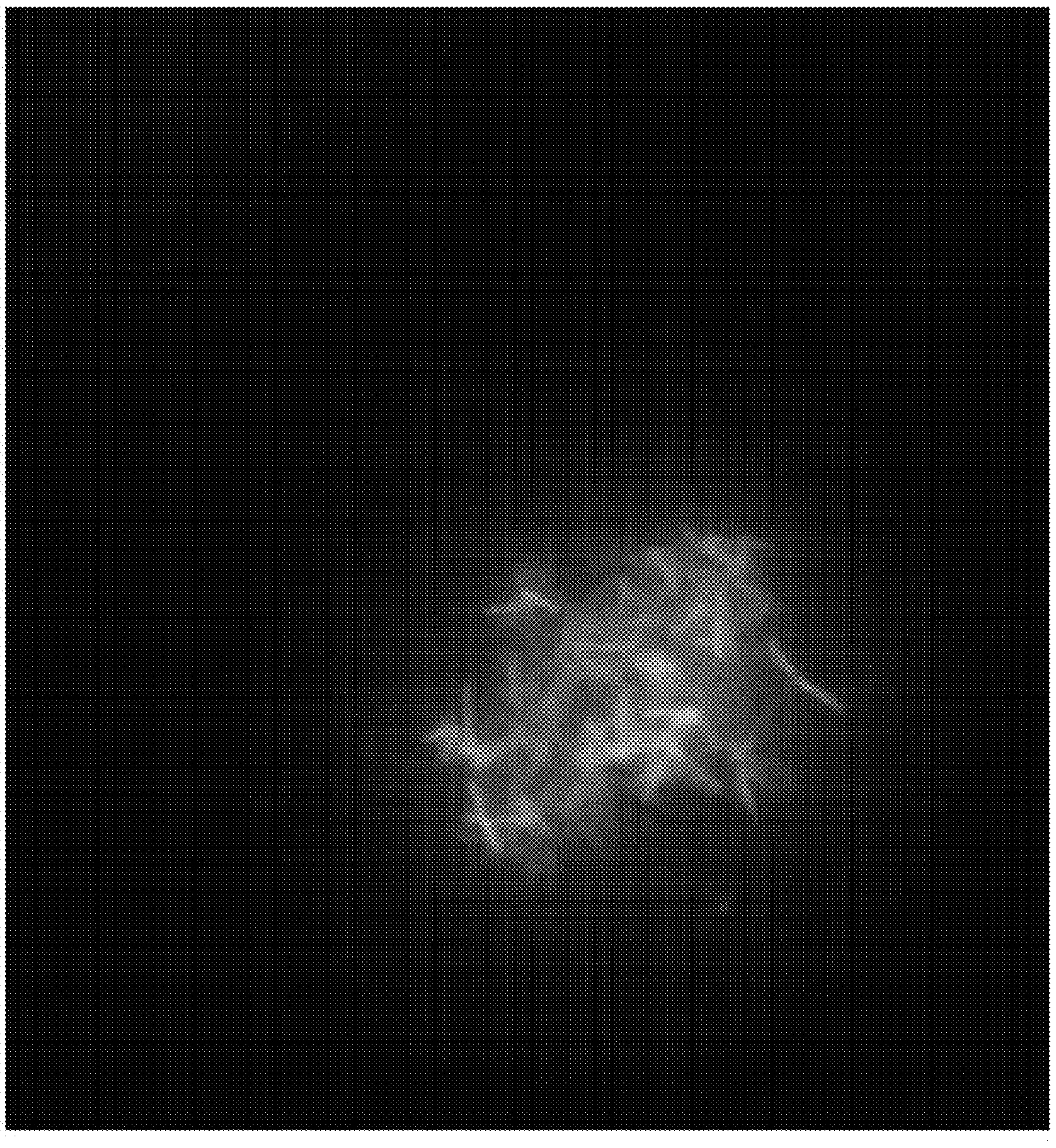
FIG. 11 depicts an exemplary Auramine Stain of MAP culture from human PBL grown by Tika Culture.
Figure 12:
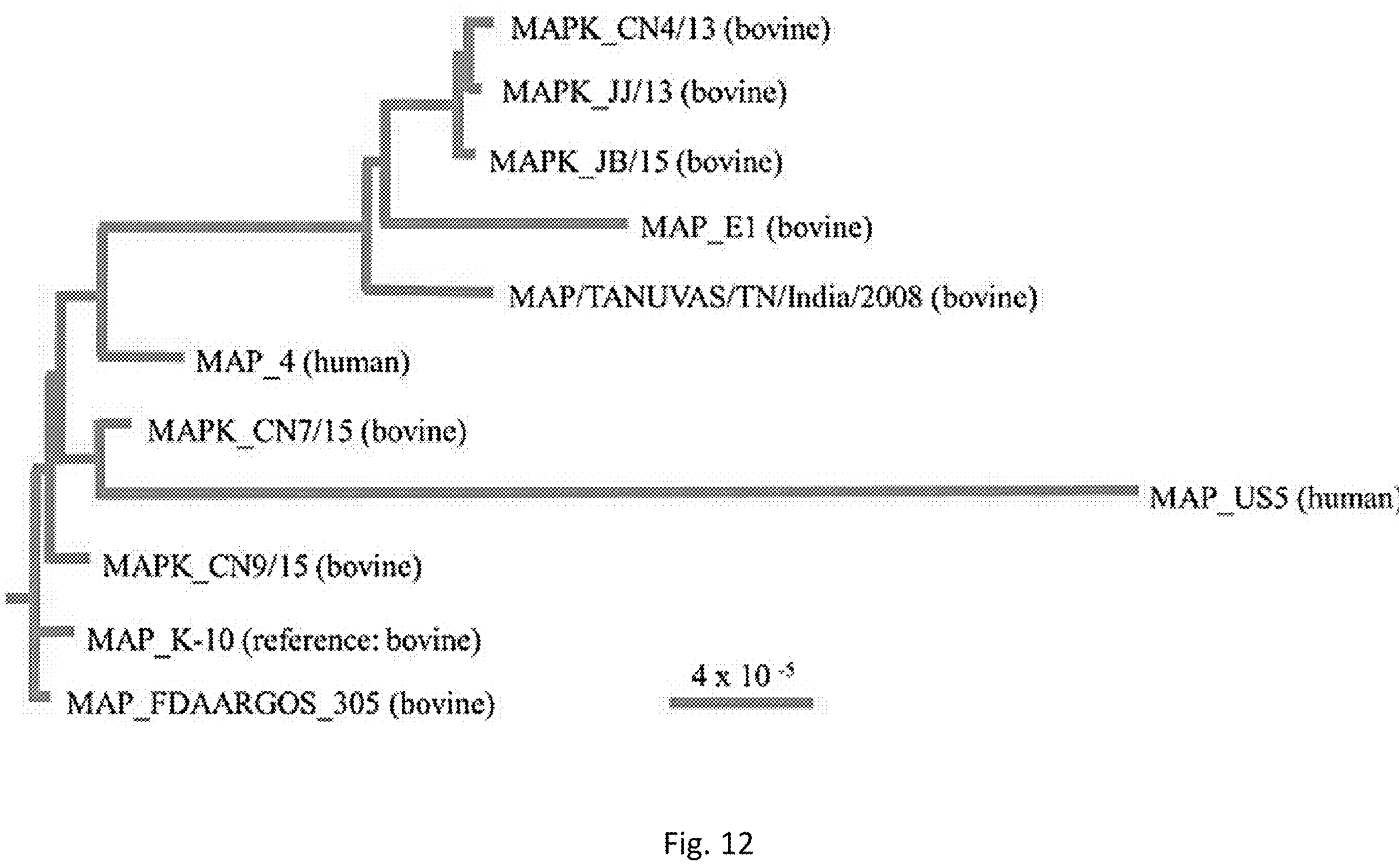
FIG. 12 depicts a dendrogram of MAP Isolate. Shown is a phylogenetic tree representing the relationship of MAP strain US5 recovered from one subject (US5) who had a concurrent sample that was positive on the phage assay to nine assembled MAP genomes of bovine and one of human origin available at NCBI. Scale bar is representative of the frequency of variation per site across compared across the genomes of the other strains displayed on this phylogenetic tree.

Definite identification of one viable isolate recovered from the blood of a single subject with IBS was confirmed as MAP by whole genome sequencing (WGS) and an assembled contiguous sequence compared with MAP isolates in a large genome bank. The isolate phage, TiKa culture isolate and WGS dendrogram are shown in FIG. 10, FIG. 11 and FIG. 12, respectively.

The conclusions of the present Example are now described herein.

This Example definitively demonstrates viable MAP organisms to be present in the blood of a significantly high number of humans and that this state of infection can be persistent. Viable MAP bacteremia was not exclusive to any one of the groups tested including patients with CD, UC, CD with UC, a range of other autoimmune diseases or asymptomatic subjects.

The study has compared three culture methods and a phage based plus culture method, tested blinded and in parallel on aliquoted samples of blood buffy coats processed at differing laboratories with expertise in using each method. All positive MAP cultures were identified and confirmed by validated specific molecular identification using either nested IS900PCR, (Naser, S. A., et al., *Lancet,* 2004, 364: 1039-1044) or IS900 plus MAP gene F57 PCRs (Bull, T. J., et al., *J Clin Microbiol,* 2003, 41: 2915-2923). Aliquots of the same samples were studied by each of the methods, but sufficient funding was not available to perform the same methods in all laboratories. The methods selected included a MGIT culture method previously used for MAP in human PBLs advocated by Naser (Naser, S. A., et al., *The Open Inflammation Journal,* 2009, 2: 22-23) and two new culture methods; TiKa decontamination and culture (Bull, T. J., et al., *Front Microbiol,* 2016, 7: 2112) and culture in 7H9+ broth (herein referred to as Pozzato culture; Pozzato, N., et al., *J Microbiol Methods,* 2011, 84: 413-417; Grant, I. R., et al., *J Dairy Sci,* 2017, 100: 9723-9735). Culture of MAP from buffy coat white cell fractions using the MGIT method alone showed an increased correlation with CD patients compared to non-CD controls. The other two methods (TiKa and Pozzato culture), whilst also culturing MAP from a significant number of patients did not yield a significant difference between any of the groups. Previous meta-analyses (Feller and Abubakar, 2007) have indicated a higher rate of MAP detection, using molecular detection methodology in samples from CD patients compared to controls.

The culture results as a whole do not fully support this conclusion; however, these previous analyses were predominantly based on data from randomly targeted gastrointestinal mucosal biopsies, whilst the present study tested blood samples, which could account for the discrepancy. In addition, and again in parallel on blinded aliquots of samples at a separate laboratory, an optimized phage amplification assay designed to detect viable MAP was included (Foddai, A., et al., *Appl Environ Microbiol,* 2009, 75: 3896-3902). This rapid culture-based/phage amplification assay detects only viable mycobacterial cells present in samples that are able to take up and amplify mycobacterial specific phages, which then burst to release progeny phages. When released these can be plaque assayed and the plaques (containing the original lysed mycobacteria) subjected to species specific PCR to detect and quantify MAP presence within 48 hours. In this study aliquots of the phage tested samples were in addition incubated in Pozzato medium and re-tested to confirm positivity after a period of growth. This method was able to detect viable mycobacteria in samples within 2 days and importantly was also able to show that of nine patients in our study that were initially MAP positive and could be followed up after one year, all remained positive for MAP in their blood after this time.

The results show that both alternative culture approaches (TiKa and Pozzato cultures) were able to culture viable MAP more effectively than the reference MGIT method, irrespective of subject group. These findings suggest that the composition of MGIT ParaTB medium is not optimal for isolation of MAP from human PBLs. Whilst the MGIT culture approach may have yielded a greater number of MAP positive cultures from PBLs of CD patients compared to non-CD controls (the expected outcome in light of previous human PBL testing of CD patients (Naser, S. A., et al., *Lancet,* 2004, 364: 1039-1044; Naser, S. A., et al., *The Open Inflammation Journal,* 2009, 2: 22-23), a similar or higher number of non-CD controls tested positive for viable MAP than CD patients by the TiKa and Pozzato culture methods. One explanation for this observation is that MAP phenotypes, persistent in blood are not in a fully growth competent physiological state or as occurs in other mycobacterial species have entered dormancy phases. This is possibly more involved in inducing these phenotypes. Hence some form of resuscitation of MAP may be necessary before growth can occur. The differing composition of TiKa and Pozzato broths could offer a reason for this discrepancy in MAP resuscitation capability. Both are based on Middlebrook 7H9 but the TiKa system includes TiKa supplemented Pozzato culture medium followed by long term culture in TiKa supplemented MGIT culture whilst the Pozzato medium used in our study excluded the addition of egg yolk as previously described to isolate MAP from cattle faeces (Pozzato, N., et al., *J Microbiol Methods,* 2011, 84: 413-417) to allow optical density of cultures to be monitored during incubation. Further work is necessary to determine the essential ingredient in this case.

Figure 13:
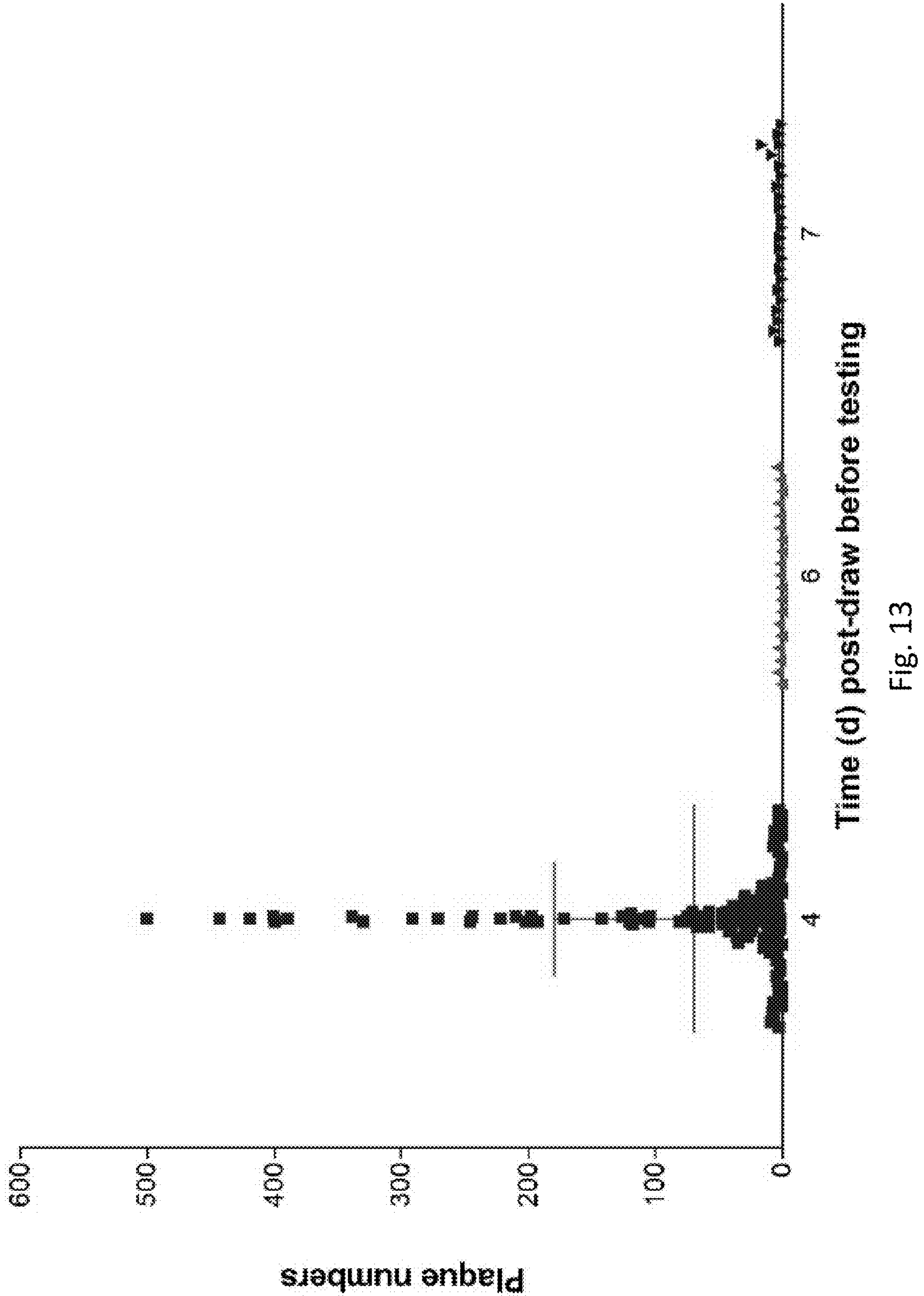
FIG. 13 depicts exemplary results demonstrating the impact of length of PBL sample transit time between blood draw in USA and commencement of testing at Queen's University Belfast, UK, on plaque numbers obtained with the phage assay. One-way ANOVA indicates significantly higher plaque numbers (p-value=0.0012) for phage assay positive PBL samples tested at 4 days post-draw compared to phage assay positive PBL samples tested at 6 or 7 dayspost-draw.

A further difference between sample testing in the each of the laboratories was the age of the PBLs at the time of culture. Sample transport times differed which could have affected the conditions to which they were exposed. It is plausible the viability of MAP cells in the PBL samples may have reduced the longer it took for transit. This is evidenced by significant differences in plaque numbers obtained with the phage assay for PBL samples that were older at the time of testing (FIG. 13). Perhaps it is beneficial to delay PBL testing for a few days to allow either resuscitation of MAP cells in the transport medium (which was MGIT medium with OADC added) or lysis of PBL cells making MAP cells more available for culture.

The results of the present Example indicate a significant percentage of subjects had MAP bacteremia, irrespective of the underlying disease and positive in more than one of the culture methods. There are three possible explanations for this finding: 1) viable MAP is passively acquired from consumed food and not immediately cleared by the host following food consumption. This explanation is unlikely because other organisms that are consumed in the diet, survive the digestive process, and cross the "leaky bowel" in IBD into the blood do not cause persistent viable bacteremia in these hosts; 2) MAP is present, persistent and viable but does not cause disease in any human host. This explanation is also unlikely since there are no previously known examples of persistent bacteremia by a known pathogen without conferring some sort of effect 3) MAP persistently infects some hosts and as a pathogen is able to influence disease processes in some susceptible human hosts. While not being bound by any particular scientific theory, the third explanation is proposed to be most likely, and suggests that MAP represents a zoonotic agent. In this case human infection resembles the known pathogenic state in cattle in which only a minority of animals (10%) develop advanced clinical JD with the majority exhibiting sub-clinical persistent infection (Magombedze, G., et al., *PLoS One,* 2013, 8: e76636). A prior study indicated a proportion of apparently healthy individuals who may have asymptomatic mycobacterial infection. In immune recognition studies (Zhang, P., et al., *Microorganisms,* 2019, 8) 2.8% of 288 healthy blood donors were positive for antibody to mycobacterial heat shock protein 65 (anti-Hsp 65 antibody), whilst 67.9% of 109 CD patients and 85.7% of Sjogren's syndrome patients were positive for anti-Hsp 65 antibody suggesting that MAP infection and immune presentation and processing is common.

This Example points to the urgent need for further in-depth MAP studies to fully explore the role of this organism in humans. An obvious area of further research is the discovery of better therapies applied in controlled clinical trials that target and attempt to eliminate MAP (Graham, D. Y., In Proceedings of Annual Scientific Meeting and Post-graduate Course (ACG), San Antonio, Texas, October 25-30, 2019). MAP culture and phage assay studies should be conducted in other diseases of unknown etiology by experts of these methods. Finally, as a minimum measure of best practice, the possibility that MAP is a zoonotic pathogen should prompt public health measures to better control JD and MAP spread into food and the environment by governments worldwide.

Figure 14A:
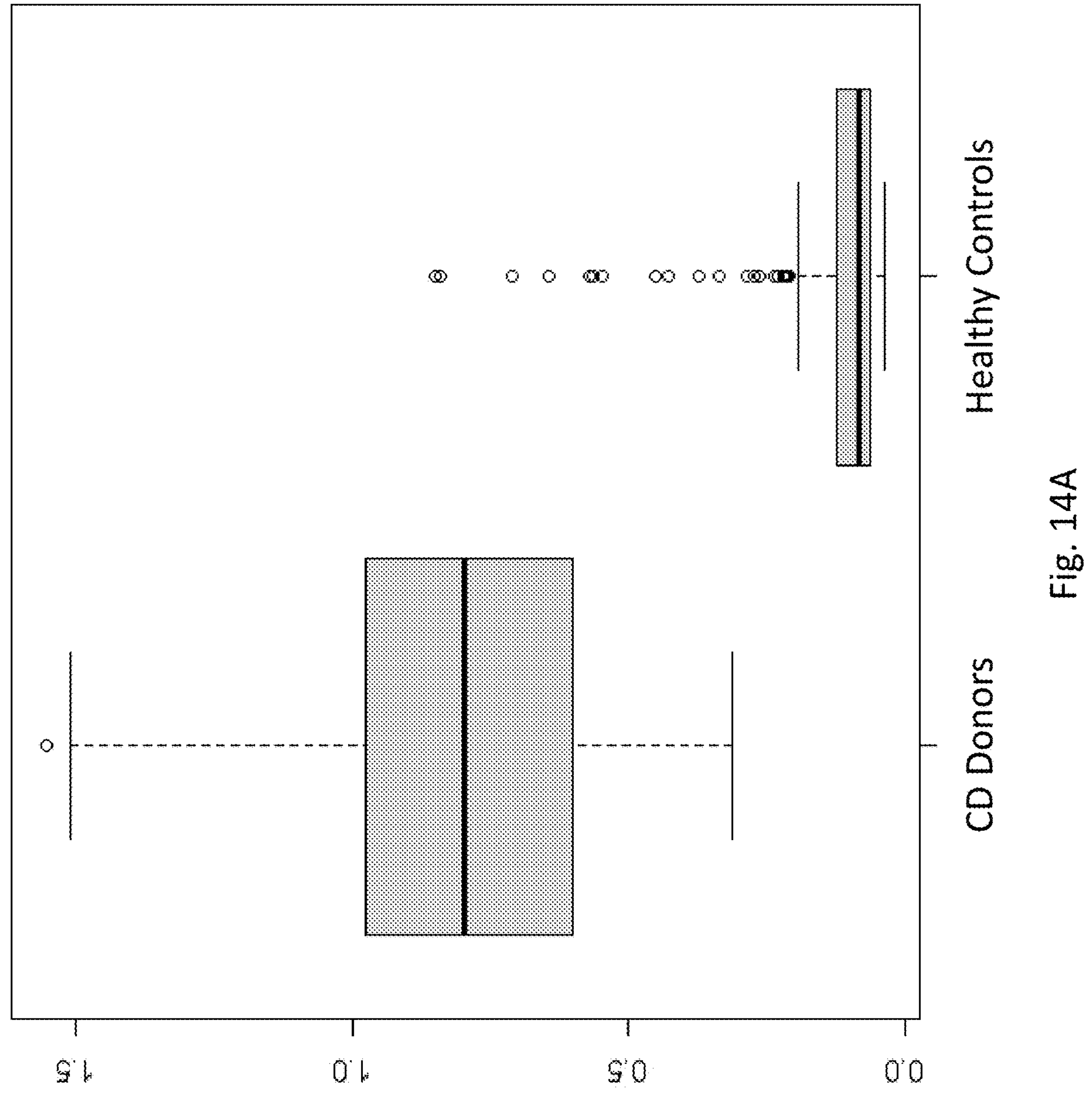
FIGS. 14A-C, depicts exemplary results demonstrating Hsp65 antibody as a robust predictor of Crohn's disease (CD).
Figure 14B:
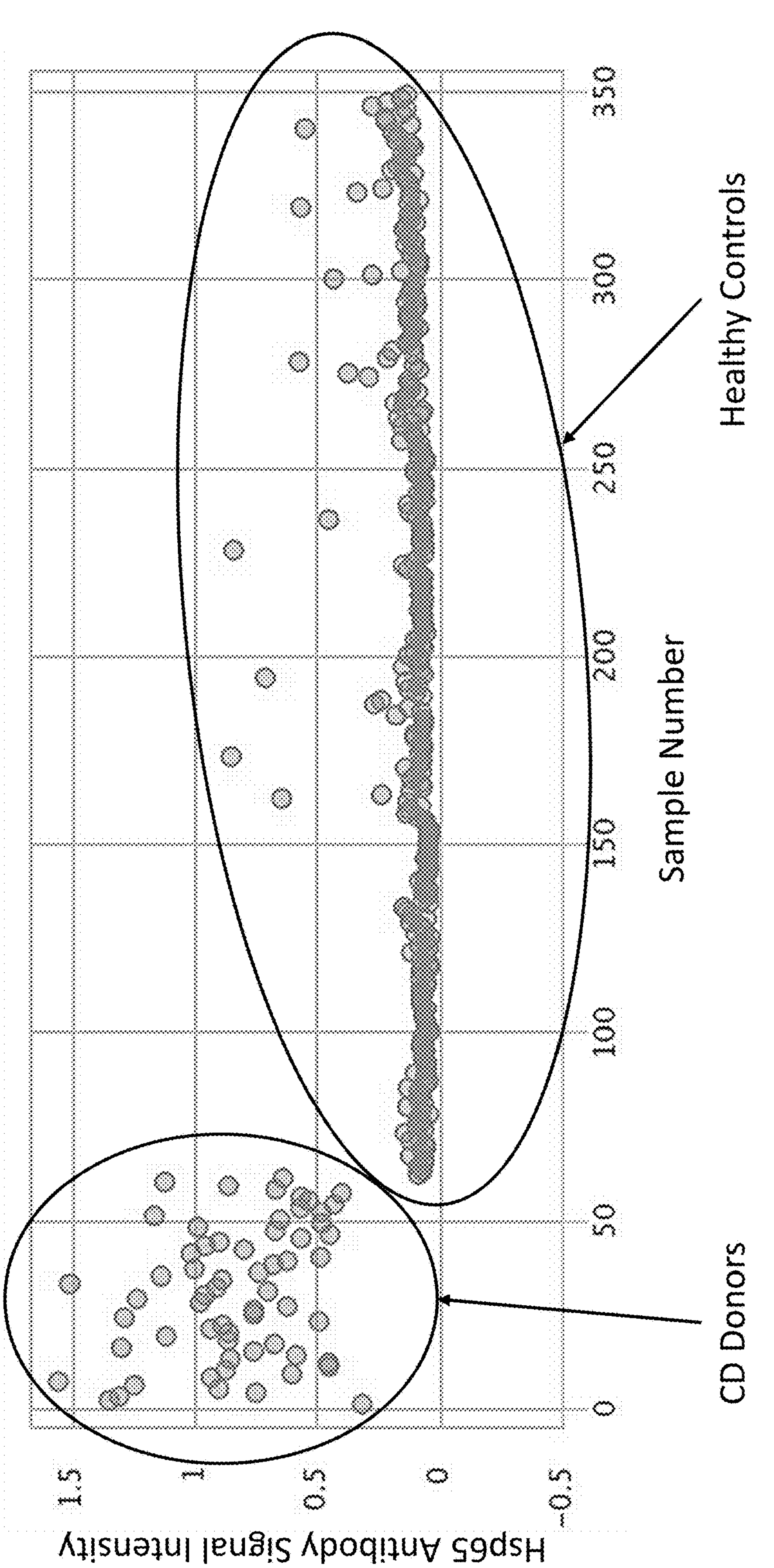
Figure 14C:
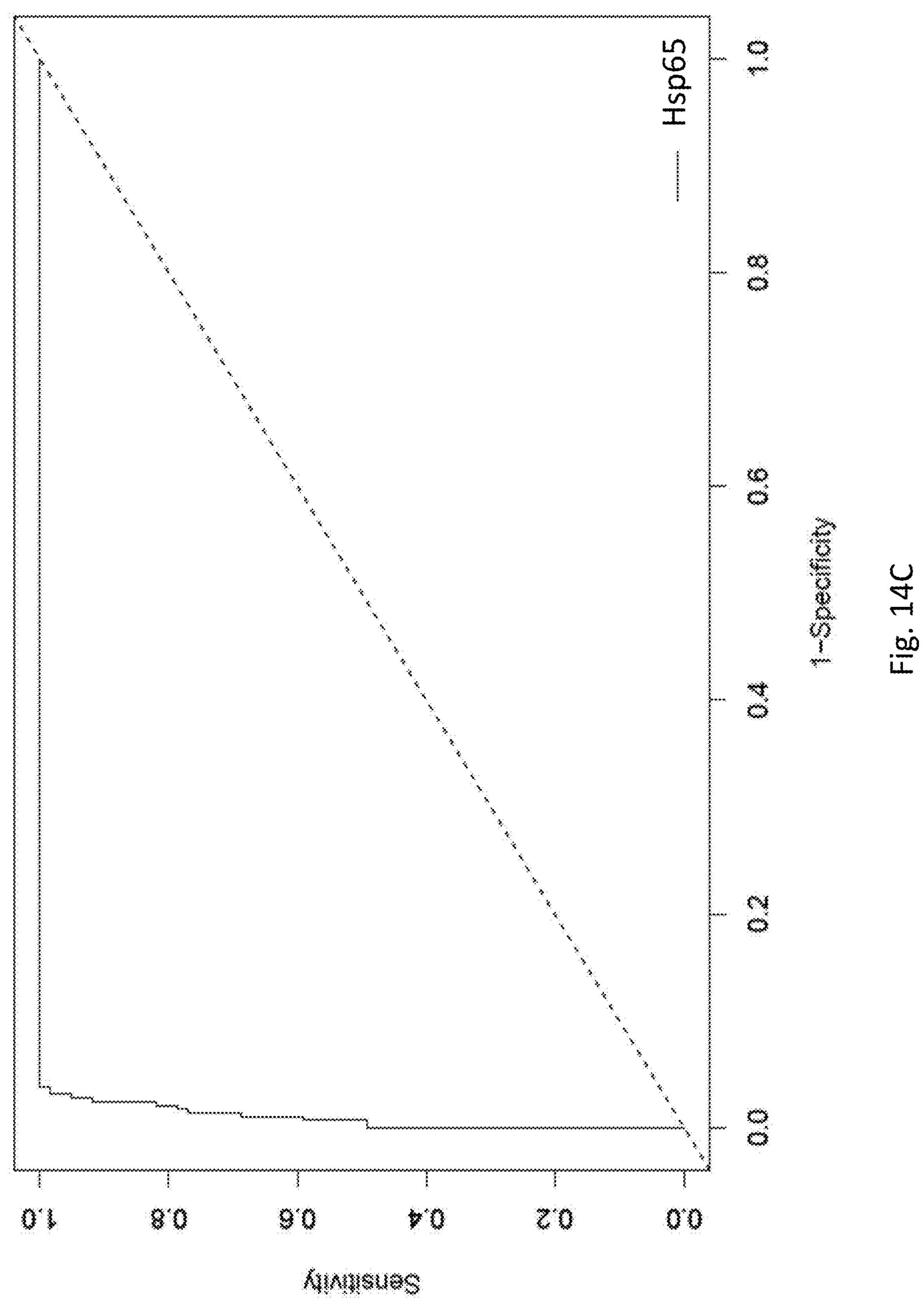

Example 2: Antibody Biomarkers Robustly Predict CD when Compared to Healthy Donors In the previous Example, all donors were recruited in a from a gastroenterology practice. As such, the donors were less healthy overall, regardless of their diagnosis for one or more inflammatory bowel diseases. To better understand the predictive power of Hsp65 antibodies as a biomarker for CD, samples from the 61 CD donors from Example 1 were compared to samples of 288 healthy Red Cross blood donors (controls). As shown in FIG. 14A, there was a highly significant difference between levels of Hsp65 antibody in CD donors as compared to controls (p-value<0.00001). Furthermore, a logistic regression yielded a C-statistic of 0.9912341 (FIG. 14B). Values for this measure range from 0.5 to 1.0, with a value of 1.0 indicating that the model perfectly identifies those within a group, suggesting that Hsp65 antibody is an excellent predictor of CD. Additionally, the area under the receiver operating characteristic (ROC) curve (AUC) was 0.99123 (FIG. 14C; p-value<0.00001). The ROC summarizes the model's performance by evaluating the trade-offs between true positive rate (sensitivity) and false positive rate (1-specificity) with a maximum value of 1.0 suggesting perfect prediction, once more indicating that the logistic regression model accurately predicts the classification of CD vs non-CD based on the Hsp65 antibody signal. Finally, an analysis showing 51 True Positives (TP; predicted CD, actual CD) and 281 True Negatives (TN; predicted non-CD; actual non-CD), suggested the following point estimates (95% CI): Sensitivity: 0.84 (0.72, 0.92), Specificity: 0.98 (0.95, 0.99), Positive predictive value: 0.88 (0.77, 0.95), and Negative predictive value: 0.97 (0.94, 0.98). Thus, Hsp65 antibodies serve as a robust marker to predict CD.

While the predictive power of Hsp65 antibody alone appears robust, Pinsky and Zhu have demonstrated that combining a positively correlated primary marker with a negatively correlated marker always increases the AUC, thus improving the predictive power of the resulting biomarker panel (*Biomarker Insights,* 2011:6 83-93). Therefore, while not being bound by any particular theory, it is believed that the ability to predict MAP infection and associated CD can be further enhanced by combining a marker that positively correlates with CD, such as Hsp65 antibodies, with a marker that negatively correlates with CD, such as PknG antibodies described in Example 1 above. Additionally, a MAP specific biomarker, such as antibodies against MAP lipopentapetide (L5P), would be useful for detecting the presence MAP infection (active or remote) irrespective of any diagnosed disease.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of diagnosing one or more autoimmune disease or disorder in a subject, the method comprising the steps of:

a) obtaining a blood sample from said subject;

b) detecting a *Mycobacterium avium* subspecies paratuberculosis (MAP) infection in said subject; detecting a first biomarker positively correlated with said autoimmune disease or disorder; and detecting a second biomarker negatively correlated with said autoimmune disease or disorder; thereby diagnosing said subject with said autoimmune disease or disorder; and c) administering to said subject diagnosed with said autoimmune disease or disorder a therapeutic to treat said autoimmune disease or disorder;

wherein the subject is a human;

wherein said one or more autoimmune disease or disorder is Crohn's Disease (CD), Ulcerative Colitis (UC), or a combination thereof;

wherein said first biomarker is an antibody specific for Hsp65; and wherein said second biomarker is an antibody specific for protein kinase G (PknG).

2. The method of claim 1, wherein said autoimmune disease or disorder is CD.

3. The method of claim 1, wherein said detecting of a MAP infection further comprises measuring one or more selected from the group consisting of: an antibody specific for L5P, L5P, and a nucleic acid encoding L5P.

4. A method of selecting a subject diagnosed with one or more autoimmune disease or disorder to be treated with one or more antibiotic, the method comprising the steps of:

a) obtaining a blood sample from said subject;

b) detecting a *Mycobacterium avium* subspecies paratuberculosis (MAP) infection in said subject; detecting a first biomarker positively correlated with said autoimmune disease or disorder; detecting a second biomarker negatively correlated with said autoimmune disease or disorder; thereby diagnosing said subject with said autoimmune disease or disorder;

c) detecting the presence of MAP with a clinical assay; and d) treating said subject with one or more antibiotic specific to MAP infection;

wherein the subject is a human;

wherein said one or more autoimmune disease or disorder is Crohn's Disease (CD), Ulcerative Colitis (UC), or a combination thereof;

wherein said first biomarker is an antibody specific for Hsp65; and wherein said second biomarker is an antibody specific for protein kinase G (PknG).

5. The method of claim 4, wherein said autoimmune disease or disorder is CD.

6. The method of claim 4, wherein said detecting of a MAP infection further comprises measuring one or more selected from the group consisting of: an antibody specific for L5P, L5P, and a nucleic acid encoding L5P.

7. The method of claim 4, wherein said clinical assay is one or more selected from the group consisting of: a MAP phage amplification assay, a Pozzato culture assay, a TiKa culture assay, and a Mycobacteria Growth Indicator Tube (MGIT) culture assay.

* * * * *